(12) United States Patent
Gomelsky et al.

(10) Patent No.: US 8,835,399 B2
(45) Date of Patent: Sep. 16, 2014

(54) NEAR-INFRARED LIGHT-ACTIVATED PROTEINS

(75) Inventors: Mark Gomelsky, Laramie, WY (US); Min-Hyung Ryu, Laramie, WY (US)

(73) Assignee: University of Wyoming, Laramie, WY (US)

( * ) Notice: Subject to any disclaimer, the term of this patent is extended or adjusted under 35 U.S.C. 154(b) by 29 days.

(21) Appl. No.: 13/560,645

(22) Filed: Jul. 27, 2012

(65) Prior Publication Data

US 2013/0030041 A1 Jan. 31, 2013

Related U.S. Application Data

(60) Provisional application No. 61/512,065, filed on Jul. 27, 2011.

(51) Int. Cl.
  *C12N 15/62* (2006.01)
  *C07K 19/00* (2006.01)
  *C07K 14/195* (2006.01)
  *C12N 9/64* (2006.01)

(52) U.S. Cl.
  CPC ............ *C12N 15/62* (2013.01); *C07K 14/195* (2013.01); *C07K 2319/60* (2013.01); *C12N 9/6475* (2013.01)
  USPC .......... 514/44 R; 530/350; 536/23.4; 506/10; 435/188; 435/455; 435/471

(58) Field of Classification Search
  None
  See application file for complete search history.

(56) References Cited

U.S. PATENT DOCUMENTS

| 6,858,429 B2 | 2/2005 | Quail | |
| 2006/0110827 A1* | 5/2006 | Lagarias et al. | 435/419 |
| 2010/0093051 A1 | 4/2010 | Kehoe | |

FOREIGN PATENT DOCUMENTS

WO  WO 2009/151948  12/2012

OTHER PUBLICATIONS

R. Arai et al.,Conformations of variably linked chimeric proteins evaluated by synchrotron X-ray small-angle scattering. Proteins. Dec. 1, 2004;57(4):829-38.*
Moglich, Andreas et al. (2010) "Engineered photoreceptors as novel optogenetic tools" Photochemical & PhotobiologicalSciences, 9:1286-1300.
Ryu, Min-Hyung et al. (2010) "Natural and Engineered Photoactivated Nucleotidyl Cyclases for Optogenetic Applications" Journal of Biological Chemistry, 285(53):41501-41508.
Tarutina, Marina et al. (2006) "An Unorthodox Bacteriophytochrome from *Rhodobacter sphaeroides* Involved in Turnover of the Second Messenger c-di-GMP" Journal of Biological Chemistry, 281(46):34751-34758.
Adamantidis AR, Zhang F, Aravanis AM, Deisseroth K and de Lecea L. 2007. Neural substrates of awakening probed with optogenetic control of hypocretin neurons. Nature 450, 420-424.
Airan RD, Thompson KR, Fenno LE, Bernstein H, Deisseroth K. 2009. Temporally precise in vivo control of intracellular signaling. Nature 458, 1025-1029.
Barends, T.R.M., E. Hartmann, J. Griese, N.V. Kirienko, D.A. Ryjenkov, J. Reinstein, R.L. Shoeman, M. Gomelsky, I. Schlichting. 2009. Structure and mechanism of a light-regulated cyclic nucleotide phosphodiesterase. Nature 459, 1015-1018.
Bhoo, S-H, Davis, SJ, Walker, J., Karniol B, Vierstra R. 2001. Bacteriophytochromes are photochromic histidine kinases using a biliverdin chromophore, Nature 414, 776-779.
Bruder, S., J.U. Linder, S.E. Martinez, N. Zheng, J.A. Beavo, and J.E. Schultz. 2005. The cyanobacterial tandem GAF domains from the CyaB2 adenylyl cyclase signal via both cAMP-binding sites. Proc Natl Acad Sci U S A. 102, 3088-92.
Bulina ME, Chudakov DM, Britanova OV, Yanushevich YG, Staroverov DB, Chepurnykh TV, Merzlyak EM, Shkrob MA, Lukyanov S, Lukyanov KA. 2006 A genetically encoded photosensitizer. Nat Biotechnol 24, 95-9.
Byrnes KR, Waynant RW, Ilev IK, Wu X, Barna L, Smith K, Heckert R, Gerst H, Anders JJ. 2005. Light promotes regeneration and functional recovery and alters the immune response after spinal cord injury. Lasers Surg Med. 36,171-85.
Cardin JA, Carlén M, Meletis K, Knoblich U, Zhang F, Deisseroth K, Tsai LH and Moore CI. 2009. Driving fast-spiking cells induces gamma rhythm and controls sensory responses. Nature 459, 663-667.
Cho M-H, Yoo Y, Bhoo S-H, Lee, S-W. Feb. 12, 2011. Purification and Characterization of a Recombinant Bacteriophytochrome of *Xanthomonas oryzae* pathovar oryzae. Protein J (2011) 30:124-131.
Crawford ED and Wells JA. 2011. Caspase substrates and cellular remodeling. Annu Rev Biochemistry 80: 1055-1087 De N, Navarro MV, Raghavan RV, Sondermann H. 2009. Determinants for the activation and autoinhibition of the diguanylate cyclase response regulator WspR. J Mol Biol 393, 619-633.

(Continued)

*Primary Examiner* — Kevin Hill
*Assistant Examiner* — Arthur S Leonard
(74) *Attorney, Agent, or Firm* — Swanson & Bratschun, L.L.C.

(57) ABSTRACT

Methods and constructs are provided for controlling processes in live animals, plants or microbes via genetically engineered near-infrared light-activated or light-inactivated proteins including chimeras including the photosensory modules of bacteriophytochromes and output modules that possess enzymatic activity and/or ability to bind to DMA, RNA, protein, or small molecules. DNA encoding these proteins are introduced as genes into live animals, plants or microbes, where their activities can be turned on by near-infrared light, controlled by the intensity of light, and turned off by near-infrared light of a different wavelength than the activating light. These proteins can regulate diverse cellular processes with high spatial and temporal precision, in a nontoxic manner, often using external light sources. For example, near-infrared light-activated proteins possessing nucleotidyl cyclase, protein kinase, protease, DNA-binding and RNA-binding activities are useful to control signal transduction, cell apoptosis, proliferation, adhesion, differentiation and other cell processes.

16 Claims, 11 Drawing Sheets

(56) References Cited

OTHER PUBLICATIONS

De N, Nevarro MV, Raghavan RV, Sondermann H. 2009 Determinants for the Activation and Autoinhibition of the Diguanylate Cyclase Response Regulator WspR. J. Mol. Biol. 393, 619-633.
De N, Pirruccello M, Krasteva PV, Bae N, Raghavan RV, Sondermann H. 2008 Phosphorylation-independent regulation of the diguanylate cyclase WspR. PLoS Biol 6, e67.
Desmet KD, Paz DA, Corry JJ, Eells JT, Wong-Riley MT, Henry MM, Buchmann EV, Connelly MP, Dovi JV, Liang HL, Henshel DS, Yeager RL, Millsap DS, Lim J, Gould LJ, Das R, Jett M, Hodgson BD, Margolis D, Whelan HT. 2006. Clinical and experimental applications of NIR-LED photobiomodulation. Photomed Laser Surg 24,121-128.
Fang Q, Carp SA, Selb J, Boverman G, Zhang Q, Kopans DB, Moore RH, Miller EL, Brooks DH, Boas DA. 2009. Combined optical imaging and mammography of the healthy breast: optical contrast derived from breast structure and compression. IEEE Trans Med Imaging 28, 30-42.
Georgianna WE, Deiters A. 2010. Reversible light switching of cell signalling by genetically encoded protein dimerization. Chembiochem;11:301-3.
Gradinaru V, Mogri M, Thompson KR, Henderson JM and Deisseroth K. 2009. Optical deconstruction of parkinsonian neural circuitry. Science 324,354-359.
Gradinaru V, Zhang F, Ramakrishnan C, Mattis J, Prakash R, Diester I, Goshen I, Thompson KR, Deisseroth K. 2010. Molecular and cellular approaches for diversifying and extending optogenetics. Cell 141, 154-65.
Jacobson K, Rajfur Z, Vitriol E and Klaus H. Chromophore-assisted laser inactivation in cell biology. Trends Cell Biology 18, 434-450.
Kuzin A, Chen Y, Seetharaman J, Mao M, Xiao R, Ciccosanti C, Foote EL, Wang H, Everett JK, Nair R, Acton TB, Rost B, Montelione GT, Tong L, Hunt JF. 2009. X-Ray Structure of Protein (EAL/GGDEF domain protein) from *M. capsulatus*, Northeast Structural Genomics Consortium Target McR174C. PDB 3ICL.
Landry Y, Niederhoffer N, Sick E, Gies JP Heptahelical and other Gprotein-coupled receptors (GPCRs) signaling. Curr Med Chem 2006, 13:51-63.
Leung DW, Otomo C, Chory J, Rosen MK. 2008 Genetically encoded photoswitching of actin assembly through the Cdc42-WASP-Arp2/3 complex pathway. Proc Natl Acad Sci U S A. 105, 12797-802.
Levskaya A, Chevalier AA, Tabor JJ, Simpson ZB, Lavery LA, Levy M, Davidson EA, Scouras A, Ellington AD, Marcotte EM, Voigt CA. 2005. Synthetic biology: engineering *Escherichia coli* to see light. Nature 438, 441-442.
Levskaya A, Weiner OD, Lim WA, Voigt CA. 2009. Spatiotemporal control of cell signalling using a light-switchable protein interaction. Nature 461, 997-1001.
Li P, Gao X-G, Arellano RO, Renugopalakrishnan V. 2001. Glycosylated and Phosphorylated Proteins—Expression in Yeast and Oocytes of *Xenopus*: Prospects and Challenges—Relevance to Expression of Thermostable Proteins. Protein Expression and Purification, 22, 369-380.
Liu X and Tonegawa S. 2010. Optogenetics 3.0. Cell 141, 22-24.
Mackenzie SH and Clay C. 2008. Targeting cell death in tumors by activating caspases. Curr Cancer Drg Targets 8, 190-209.
Maheshwari SC, Khurana JP, Sopory SK. 1999 Novel light-activated protein kinases as key regulators of plant growth and development. J. Biosci. 24 No. 4 49-514.
Miesenböck G. The optogenetic catechism. 2009. Science 326, 395-9.
Möglich A, Ayers RA, Moffat K. 2009. Design and signaling mechanism of light-regulated histidine kinases. J Mol Biol 385, 1433-44.
Möglich A, Moffat K. Sep. 2010. Engineered photoreceptors as novel optogenetic tools. Photochemical and Photobiological Sciences, 9, 1286-1300.
Möglich A, Yang X, Ayers RA, Moffat K. 2010. Structure and function of plant photoreceptors. Annu Rev Plant Biol 61, 21-47.
Pei J, Grishin NV. 2001. GGDEF domain is homologous to adenylyl cyclase. Proteins. 42, 210-216.
Pop C., Feeney, A. Tripathy, and A.C. Clark. 2003. Mutations in the procaspase-3 dimer interface affect the activity of the zymogen. Biochemistry, 42, 12311-12320.
Rockwell NC, Su YS, Lagarias JC. 2006. Phytochrome structure and signaling mechanisms Annu Rev Plant Biol. 57, 837-858.
Ryjenkov, D.A., M. Tarutina, O.V. Moskvin and M. Gomelsky. 2005. Cyclic diguanylate is a ubiquitous signaling molecule in bacteria: Insights into the biochemistry of the GGDEF protein domain. J Bacteriol 187, 1792-1798.
Ryu, M.-H., O.V. Moskvin, J Siltberg-Liberles, and M. Gomelsky. 2011. Natural and engineered photoactivated nucleotidyl cyclases for optogenetic applications. J Biol Chem Oct. 28, 2010. [Epub ahead of print].
Schirmer T, Jenal U. 2009. Structural and mechanistic determinants of c-di-GMP signalling. Nat Rev Microbiol 7, 724-735.
Shu X, Royant A, Lin MZ, Aguilera TA, Lev-Ram Varda, Steinbach PA, Tsien RY. 2009. Mammalian expression of infrared fluorescent proteins engineered from a bacterial phytochrome. Science 324, 804-7.
Sinha SC, Sprang SR. 2006. Structures, mechanism, regulation and evolution of class III nucleotidyl cyclases. Rev Physiol Biochem Pharmacol 157,105-140.
Sjulson L and Miesenböck G. 2008. Photocontrol of neural activity: Biophysical mechanisms and performance in vivo. Chem. Rev 108, 1588-1602.
Sohal VS, Zhang F, Yizhar O and Deisseroth K. 2009. Parvalbumin neurons and gamma rhythms enhance cortical circuit performance, Nature 459, 698-702.
Sorokina O, Kapus A, Terecske K, Dixon LE, Kozma-Bognar L, Nagy F, and Millar AJ. 2009. A switchable light-input, light-output system modelled and constructed in yeast. Journal of Biological Engineering, 3:15.
Stierl M, Stumpf P, Udwari D, Gueta R, Hagedorn R, Losi A, Gärtner W, Petereit L, Efetova M, Schwarzel M, Oertner TG, Nagel G, Hegemann P. Light modulation of cellular cAMP by a small bacterial photoactivated adenylyl cyclase, bPAC, of the soil bacterium *Beggiatoa*. J Biol Chem. 2011, 286:1181-8.
Strickland D, Moffat K, Sosnick TR. 2008. Light-activated DNA binding in a designed allosteric protein. Proc Natl Acad Sci U S A 105, 10709-10714.
Tarutina, M., Ryjenkov, D.A., and Gomelsky, M. 2006. An unorthodox bacteriophytochrome from *Rhodobacter sphaeroides* involved in turnover of the second c-di-GMP. J Biol Chem 281, 34751-34758, 2006.
Toettcher JE, Voigt CA, Weiner OD, and Lim WA. 2011. The promise of optogenetics in cell biology: interrogating molecular circuits in space and time. Nature Methods 8, 35-38.
Tønnesen J, Sørensen AT, Deisseroth K, Lundberg C and Kokaia M. 2009. Optogenetic control of epileptiform activity, Proc Natl Acad Sci USA 106, 12162-12167.
Tsai HC, Zhang F, Adamantidis A, Stuber GD, Bonci A, de Lecea L, and Deisseroth K. 2009. Phasic firing in dopaminergic neurons is sufficient for behavioral conditioning. Science 324, 1080-1084.
Tyszkiewicz AB, Muir TW. 2008. Activation of protein splicing with light in yeast. Nature Methods 5, 303-305.
Vera , Aris A, Daura X, Martinez MA, Villaverde A. 2005. Engineering the *E. coli* beta-galactosidase for the screening of antiviral protease inhibitors. Biochem Biophys Res Commun 329, 453-6.
Vuillet L, Kojadinovic M, Zappa S, Jaubert M, Adriano J.M., Fardoux JI, Hannibal L, Pignol D, Vermeglio A, Giraud E. 2007. Evolution of a bacteriophytochrome from light to redox sensor. EMBO Journal, 26, 3322-3331.
Wu YI, Frey D, Lungu O., Jaehrig A, Schlichting I, Kuhlman B, Hahn KM. 2009. A genetically encoded photoactivatable Rac controls the motility of living cells. Nature 461,104-108.
Yang X, Kuk J, Moffat K. 2008. Crystal structure of *Pseudomonas aeruginosa* bacteriophytochrome: photoconversion and signal transduction. Proc Natl Acad Sci U S A 105, 14715-14720.
Yang X, Kuk J, Moffat K. 2009. Conformational differences between the Pfr and Pr states in *Pseudomonas aeruginosa* bacteriophytochrome. Proc Natl Acad Sci U S A 106, 15639-15644.

(56) References Cited

OTHER PUBLICATIONS

Yazawa M, Sadaghiani AM, Hsueh B, Dolmetsch RE. 2009. Induction of protein-protein interactions in live cells using light. Nat Biotechnol 27, 941-945.

Zimmer M. 2009. GFP: from jellyfish to the Nobel prize and beyond. Chem Soc Rev 38, 2823-2832.

Cho M-H, Yoo Y, Bhoo S-H, Lee, S-W. Feb. 12, 2011. Purification and Characterizationcharacterization of a Recombinant Bacteriophytochromerecombinant bacteriophytochrome of *Xanthomonas oryzae* pathovar oryzae. Protein J (2011) 30:, 124-131.
Cubeddu R, Pifferi A, Taroni P, Torricelli A, Valentini G. 1999. Noninvasive absorption and scattering spectroscopy of bulk diffusive media: An application to the optical characterization of human breast. Appl Phys Lett 74, 874-6.
Gomelsky, M and Hoff WH. 2011. Light helps bacteria make important lifestyle decisions. Trends Microbiol 19, 441-8.
Hayashi H, Cuddy M, Shu VC, Yip KW, Madiraju C, Diaz P, Matsuyama T, Kaibara M, Taniyama K, Vasile S, Sergienko E, Reed JC. 2009. Versatile assays for high throughput screening for activators or inhibitors of intracellular proteases and their cellular regulators. PLoS One 4, e7655.
Iseki M, Matsunaga S, Murakami A, Ohno K, Shiga K, Yoshida K, Sugai M, Takahashi T, Hori T, Watanabe M. 2002. A blue-light-activated adenylyl cyclase mediates photoavoidance in *Euglena gracilis*. Nature. 415, 1047-51.
Mills E, Chen X, Pham E, Wong SS, and Truong K. 2012. Engineering a photoactivated caspase-7 for rapid induction of apoptosis. ACS Synthetic Biol 3, 75-82.
Serezani CH, Ballinger MN, Aronoff DM, Peters-Golden M. 2008. Cyclic AMP: master regulator of innate immune cell function. Am J Respir Cell Mol Biol. 39, 127-32.
Walters J, Pop C, Scott FL, Drag M, Swartz P, Mattos C, Salvesen GS, Clark AC. 2009. A constitutively active and uninhibitable caspase-3 zymogen efficiently induces apoptosis. Biochem J 424, 335-45.
Wan S, Parrish JA, Anderson RR, Madden M. 1981. Transmittance of nonionizing radiation in human tissues. Photochem Photobiol 34, 679-81.
Weissleder R. 2001. A clearer vision for in vivo imaging. Nature Biotechnol 19, 316-7.

* cited by examiner

US 8,835,399 B2

NEAR-INFRARED LIGHT-ACTIVATED PROTEINS

CROSS-REFERENCE TO RELATED APPLICATIONS

This application claims priority to U.S. Provisional Patent Application No. 61/512,065 filed Jul. 27, 2011, which is incorporated herein by reference to the extent not inconsistent herewith for purposes of written description and enablement.

STATEMENT REGARDING FEDERALLY SPONSORED RESEARCH

This invention was made with Government support under NIH Contracts No. 2P20 RROI6474-09 and 1R21CA167862-01. The Government has certain rights in the invention.

BACKGROUND

Light-activated fluorescent proteins have revolutionized imaging technologies, and with them our fundamental understanding of cellular processes (Zimmer, 2009). The use of light to control protein activities in live animals with spatiotemporal resolution unmatched by drugs has even greater potential (Miesenböck et al. 2009; Liu & Tonegawa, 2010). Optogenetic approaches utilizing natural photoreceptors have provided insights into the underpinnings of information processing in the nervous system, locomotion, awakening, neural circuits in Parkinson's disease, progression of epilepsy, etc. (Airan et al., 2009; Adamantidis et al., 2007; Cardin et al., 2009; Gradinaru et al., 2009; Sohal et al., 2009; Tønnesen et al., 2009; Tsai et al., 2009; and Gradinaru et al., 2010). Several groups have succeeded in engineering photoactivated proteins with new functions (Mills et al., 2012; Strickland et al., 2008; Tyszkiewicz and Muir, 2008; Yazawa et al., 2009; Möglich et al., 2009; Wu et al., 2009; and Georgianna & Deiters, 2010). However, the use of optogenetic approaches outside neurobiology remains very limited (reviewed in Möglich et al., 2010; Toettcher et al., 2011). The potential of using proteins activated by far-red and near-infrared (NIR) light, which penetrates animal tissues to the depths of several centimeters (Cuberddu et al., 1999; Wan et al., 1981; Byrnes et al., 2005) and therefore can be applied externally, has remained largely unexplored because of limitations in the ability to engineer such proteins with desired output activities.

SUMMARY

The ability to precisely activate or inactivate desired proteins in vivo—in specific cells or tissues of live animals, during normal or disease conditions—offers unprecedented insights into understanding diverse-biological processes. However, current genetic and pharmaceutical approaches do not provide the spatiotemporal resolution and/or target specificity to accurately interrogate cellular functions in real time in vivo.

Light has emerged as an alternative means to control cellular activities with spatiotemporal precision unattainable by other approaches. The recently emerged field of optogenetics involves delivery into model organisms of recombinant genes encoding proteins that can be turned "on" and "off" by light. While natural photoactivated proteins (e.g., channelrhodopsins) have revolutionized neurobiology, the enormous potential of engineered photoactivated proteins remains largely untapped. We have elucidated principles of engineering far-red/NIR light-activated proteins using photosensory modules of bacteriophytochromes, a subclass of phytochromes containing the biliverdin IXα chromophore (Rockwell & Lagarias, 2006). Far-red/NIR light penetrates animal tissues much deeper (centimeter scale) than visible light (millimeter scale) absorbed by currently used photoreceptors; therefore bacteriophytochromes are particularly attractive and potentially transformative for optogenetic applications in mammalian models of development and disease as well as for disease treatment.

Applicants have designed bacteriophytochrome-based homodimeric photoactivated proteins and provide principles for engineering a broad spectrum of photoactivated functions. A large fraction of important signal transduction proteins operate as homodimers, e.g., membrane receptors, protein kinases, protein phosphatases, proteases, nucleases, and transcription factors. Three-dimensional structures of many of these proteins are known to the art. All these proteins represent targets for protein engineering.

"Transplantation" of a phytochrome photoreceptor module has been achieved previously, albeit only to homologous downstream domains (Levskaya et al., 2005, 2009). Phytochromes have also been designed to control protein-protein interactions in a light-dependent manner (Leung et al., 2008). However, the present disclosure is the first to provide photosensory modules of bacteriophytochromes to directly activate heterologous outputs. No such engineered modules have previously been available, and specifically, no light-activated bacteriophytochrome-based nucleotidyl cyclases or caspases have previously been available.

Provided herein are methods of controlling processes in live animal, plant or microbialorganisms via genetically engineered far-red/NIR-light activated homodimeric proteins, NIRLAHPs. These proteins are chimeras comprised of photosensory modules of bacteriophytochromes that are activated (or inactivated) by far-red/NIR light and output modules that possess enzymatic activity and/or ability to bind to DNA, RNA, protein, or small molecules.

In this application, the term "NIR light" is used to describe light of 700-3000 nm wavelengths, commonly defined as NIR or infra-red A (IR-A), as well as an adjacent region of far-red light of 650-700 nm wavelengths.

Genes encoding NIRLAHPs can be introduced into live animals, plants or microbes, where their activities can be turned on by NIR light, controlled by the duration and/or intensity of light, and turned off by light of a different wavelength than the activating light. By using NIRLAHPs one can regulate diverse cellular processes with high spatial and temporal precision in a nontoxic manner, often using external light sources. For example, NIRLAHPs possessing nucleotidyl cyclase, protein kinase, protease, DNA-binding and RNA-binding activities can be used to control metabolic enzymes, signal transduction, cell, apoptosis, proliferation, adhesion, differentiation and other processes. These features of NIRLAHPs can be used in various medical applications. For example, a NIR light-activated executor (effector) caspase can be introduced into tumors (or other kinds of disease-causing cells, e.g., cells carrying viruses) to induce an apoptotic cell death pathway, thus providing a noninvasive gene therapy of cancer (or viral diseases). Human cells expressing hormones (e.g., insulin) can be regulated by NIRLAHPs (e.g., due to the light-regulated gene expression or hormone-synthesizing activity) and can be used to treat hormone deficiencies (e.g., diabetes). NIRLAHPs can be used to photoactivate immune cells at desired locations (e.g., tumor or infection sites). NIRLAHPs can also be used to convert prodrugs into active drugs in irradiated tissues and/or organs. NIRLAHPs expressed in bacteria (e.g., *E. coli* or *Lactobacillus*) that belong to normal human or animal microflora can be used to photoactivate organ-localized (e.g., colon, vagina) synthesis of bacteriophages, antibiotics, and other drugs to target pathogenic microorganisms, polyps and tumors or to produce probiotics. Some NIRLAHPs can be used as protein-based drugs directly (e.g., by light-activated binding and control of cellular receptors). NIRLAHPs can also be used in cell-based nanomanufacturing (by virtue of light-dependent cell growth or light-dependent production of a desired product), and in industrial applications (e.g., light-induced dissolution of bacterial biofilms formed in the presence of engineered near-infrared light-sensitive cells that secrete biofilm-dispersion agents):

The principal advantages of NIR light over ultraviolet (UV) and visible light, which are sensed by all other types of photoreceptor proteins, is superior penetration into biological tissues (centimeter scale) and lack of toxicity. Therefore, activities of NIRLAHPs can be controlled in tissues that are not accessible to UV and visible light (e.g., most animal tissues); they can be controlled not only by implanted light sources, but in many cases, by external light sources (e.g., by lasers or light-emitting diodes, LEDs, placed outside organisms that are being controlled). Additional advantages of bacteriophytochrome-based NIRLAHPs involve their capacity for instant photoinactivation (usually by light of a longer wavelength than the activating light); lack of known toxicity of NIR light; and lack of toxicity, at low doses, of the chromophore biliverdin IX$\alpha$, which is naturally present in most animal tissues or can be supplied via injection, diet, or via synthesis in vivo by a heterologous heme oxygenase.

Methods are provided herein for producing photoactive fusion proteins having a desired activity controllable by NIR light, said method comprising the steps: a. designing one or more homodimeric fusion proteins, each comprising a photoreceptor protein module and a heterologous output module, wherein: i. said homodimeric fusion proteins comprise two monomers that each comprise: (1) a photoreceptor module of a bacteriophytochrome; and (2) a heterologous output module capable of being activated upon homodimerization to perform said desired activity; and ii. said monomers are not active when separated, but are capable of combining to form homodimers that are controllable by NIR light; wherein designing said fusion proteins comprises identifying candidate output domains based on 3D structures or structural models, identifying candidate protein fusion sites and estimating lengths of $\alpha$-helices linking said output modules to said photosensory modules; b. producing a plurality of DNA molecules, each encoding a said monomer of a said homodimeric fusion protein that has at least one unique fusion site; c. screening said DNA molecules for their ability to produce homodimeric photoactive fusion proteins capable of performing said desired activity by a method comprising: transforming a designed test organism with a plurality of different said DNA molecules such that different said fusion proteins are expressed in each test organism; ii. allowing the expressed fusion proteins to bind bacteriophytochrome chromophore and form homodimeric proteins; and iii. applying selected wavelengths of NIR light to said transformed organisms and determining: the level of said desired activity of said fusion proteins in said organisms in the presence and absence of said selected wavelengths of light; wherein the level of said desired activity of said fusion proteins is controllable by NIR light when the level of said desired activity is changed by the presence and/or absence of NIR light having said selected wavelengths. Controllability by NIR light of the fusion proteins exists when the fusion proteins have higher ratios of activity in the light versus dark or vice versa.

The bacteriophytochrome photoreceptor module can be from the BphG1 protein from *Rhodobacter sphaeroides*. The test organism for expression of said fusion protein can be a cultured organism selected from the group consisting of *E. coli*, yeast, plant, and animal cells selected or modified so as to detectably exhibit the level of activity of said expressed fusion protein controllable by the presence or absence of NIR light. Examples of light-activated fusion proteins produced by the methods hereof are light-responsive nucleotidyl cyclases and light-responsive uncleavable procaspase-3.

The test organisms can comprise an endogenous chromophore or they may not. If required, they are transformed with DNA encoding a heme oxygenase gene capable of being expressed therein to produce a biliverdin IX$\alpha$ chromophore, e.g. the BphO1 protein from *Rhodobacter sphaeroides*.

The method can also comprise modifying the design of the fusion proteins that are controllable by NIR light to produce additional candidate fusion proteins by designing additional fusion sites and linkers for said fusion proteins and repeating the steps of producing DNA encoding the additional fusion proteins, transforming suitable organisms with this DNA, expressing the DNA, and screening the resultant fusion proteins for additional fusion proteins controllable by NIR light. This is achieved by increasing or decreasing the lengths and amino acid sequences of the $\alpha$-helical linkers linking the photoreceptor modules with the output modules, e.g., the linker lengths can be increased or decreased by three or four amino acids.

Fusion proteins controllable by NIR light, or additional fusion proteins controllable by NIR light produced by increasing or decreasing their linker lengths, can be mutagenized to create further candidate fusion proteins controllable by NIR light, followed by repeating the screening steps to identify photoactivated fusion proteins with improved properties, e.g. low background activity and high photoactivation ratio.

In various embodiments, fusion proteins are produced by the methods hereof whose activity can be increased by the application of NIR light of a selected wavelength, or can be decreased by the application of NIR light of a selected wavelength. In embodiments, the desired activity can be gradually decreased of gradually increased by ceasing to apply NIR light of a selected wavelength or by application of NIR light of a selected wavelength.

Provided herein are homodimeric fusion proteins controllable by NIR light, said fusion proteins comprising a photoreceptor module comprising a bacteriophytochrome and a heterologous output module capable of producing a desired activity, e.g., light-activated nucleotidyl cyclases or light-activated uncleavable procaspase-3. Recombinant DNA molecules encoding the homodimeric fusion proteins hereof are also provided.

In addition, methods are provided herein for controlling an in vivo process in a host, which is a living cell or organism using the fusion proteins hereof. The method comprises: a. introducing into the cell or organism a DNA sequence encoding a homodimeric fusion protein comprising a photoreceptor module comprising a bacteriophytochrome and a heterologous output module capable of modulating said process; b. allowing said fusion protein to be expressed in said host; and c. applying NIR light of a selected wavelength to the host or preventing NIR light of a selected wavelength from reaching the host; thereby modulating the process under control of NIR light. Such processes can be selected from the group consisting of metabolic processes, signal transduction, cell apoptosis, cell proliferation, cell adhesion, and cell differentiation.

In embodiments hereof, methods hereof for producing NIRLAHPs having a desired activity controllable by NIR light comprise the steps of designing one or more homodimeric fusion proteins, each comprising a bacteriophytochrome photoreceptor module and a heterologous output module, capable of being NIR-light activated to perform said desired activity. The monomers of the fusion proteins combine spontaneously to form homodimers, and have autocatalytic activity to bind biliverdin IXα, thus forming NIRLAHPs. Designing NIRLAHPs comprises (a) identifying, based on biochemical information candidate protein output domains that function as homodimers and can be activated by homodimerization; (b) using 3D structures or building 3D models to identify optimal fusion sites and peptide linkers for attaching the heterologous output modules to the bacteriophytochrome photoreceptor modules; (c) producing a plurality of DNA molecules (a DNA library), each encoding a monomer of a homodimeric fusion protein that has at least one unique fusion site or linker sequence; and (d) screening the DNA molecules for their ability to produce homodimeric photoactive fusion proteins capable of performing the desired activity in a test organism. The screening is done by transforming a test organism designed to respond to the desired activity with the DNA constructs encoding the monomers of the homodimeric fusion proteins; allowing the expressed fusion proteins to spontaneously bind biliverdin IXα and form homodimers; applying light of selected wavelengths to the transformed organisms; and comparing the level of said desired activity of the expressed fusion proteins in the test organism in the dark and in the light. The method can then comprise (e) subjecting fusion proteins that have NIR light-activated activities identified by screening to random mutagenesis and subsequent screening (by the method described above) for mutant derivatives with improved qualities, e.g., low activity in the dark and a high light-to-dark activation ratio. The method can further comprise: (f) purification, and spectral and/or biochemical characterization of NIRLAHPs.

The optimized NIRLAHPs can be used for controlling in vivo processes in other organisms, including animals and humans, using internal and/or external sources of NIR light. The genes encoding NIRLAHPs can be introduced into the cell or organism via methods known to the art, including transformation by DNA, viral infection, and bacteriofection.

Light-activated fusion proteins, DNA molecules encoding them, and methods for using them to control processes in living hosts are also provided herein.

BRIEF DESCRIPTION OF THE DRAWINGS

The following drawings illustrate various aspects of the photoreceptor modules for optogenetic applications provided in the present disclosure.

Figure 1:
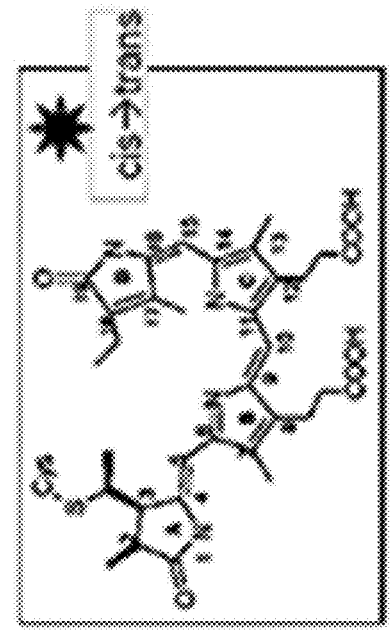
FIG. 1 shows six major photoreceptor types (Gomelsky & Hoff, 2011) (top panel) including a subclass of phytochromes known as bacteriophytochromes. The photoreceptor module from the BphG1 protein from *Rhodobacter sphaeroides* (Tarutina et al., 2006) was used into illustrate the present methods. The molecular structure of the chromophore of the BphG1 protein (biliverdin IX( ) is shown in the lower right panel. The lower left panel shows light-induced spectral changes in the BphG1 protein. The protein exists in the "dark" (Pr) form (absorption maximum 712 nm) when it is not exposed to light or irradiated with light of ~740-780 nm. Upon irradiation with light of ~650-715 nm, the protein is converted to the "lit" (Pfr) form (absorption maximum ~760 nm).
Figure 1:
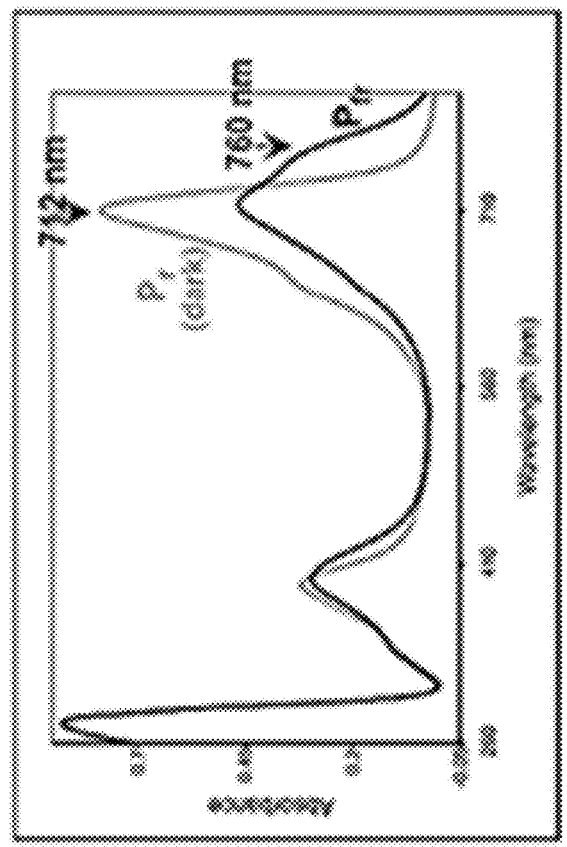

All publications and Websites disclosed herein are incorporated by reference to the extent not inconsistent herewith.

DETAILED DESCRIPTION

Definitions

Terms used herein have their generally accepted, conventional meaning in the art unless otherwise specifically defined.

A "fusion protein" hereof (also referred, to herein as an "engineered protein," a "chimeric protein" and/or a "hybrid protein") is a protein that comprises an output module and a photosensory module that do not occur together in the same protein in nature.

An "output module" (also referred to herein as an "output domain") is the portion of a protein that performs a function, e.g., enzymatic activity, or binding to DNA, RNA or another protein.

A "photosensory module" (also referred to herein as a "photoreceptor module") is a portion of a protein that contains a chromophore, through which it senses and responds to light.

A "chromophore" is a molecule bound to the photoreceptor module that serves to detect NIR light and cause a conformational change in the output domain of the fusion protein when NIR light is applied. In bacteriophytochromes, the chromophore is biliverdin IXα.

A homodimer is a protein having two identical portions (monomers) that are not linked to each other by covalent bonds but can form stable structures involving protein-protein (monomer-monomer) interactions. In the homodimeric fusion proteins hereof that are photoactive, monomers making up the homodimeric proteins are inactive until they have joined to form a particular homodimeric conformation.

Bacteriophytochromes are a subclass of phytochrome photoreceptor proteins containing biliverdin IXα as a chromophore. The photosensory modules of biliverdin IXα comprise PAS-GAF-PHY protein domains. Bacteriophytochromes covalently bind biliverdin IXα to a conserved cysteine residue via an intrinsic biliverdin ligase activity.

"Near infrared" (NIR) light is generally considered in the art to have a wavelength of between about 700-750 and about 3000 nm. "Far-red" light is generally defined as light having a wavelength at the long-wavelength red end of the visible (red) spectrum, from about 700 to about 750 nm. The visible spectrum is generally defined as having a wavelength of about 390 to about 750 nm. Bacteriophytochromes sense light from about 650 to about 800 nm, within the "NIR window" Since this "NIR window" contains light variously defined as being in the visible, far-red and NIR categories, the term "near-infrared" ("NIR") is used herein to describe light in the "NIR window" that activates bacteriophytochromes, switching them from one (dark) conformation to another (lit) conformation and back, regardless of whether the light would be generally defined as being in the NIR range, the far-red range, or in the visible range.

The term "light activation" (also referred to herein as "photoactivation") is used herein to refer to control of a protein activity by application of NIR light of selected wavelengths or removal of light from a fusion protein as described herein. The fusion protein is "activated" when NIR light applied to the photoreceptor causes a change in conformation of the output module of the fusion protein such that it changes the activity of the output module. This change is believed to be caused, at least in part, by rotation of the monomeric output modules with respect to each other such that a desired activity of the fusion protein is changed, e.g., stopped, started, enhanced, or decreased. The term "light activated" (also called "photoactive" in reference to proteins hereof) means a protein capable of being controlled by NIR light to be active or inactive, or more or less active or inactive. Thus, the terms "photoactive proteins" or "photoactivated proteins" also include "photoinactive proteins" or "photoinactivated proteins," respectively.

A "photoactivation ratio" (also referred to as a "light-activation ratio" or "dynamic range") is the ratio of protein activity upon NIR irradiation to protein activity in the dark. In embodiments, the protein activity can be achieved by applying light of selected wavelength to the protein, or by removal of such light. In embodiments, the protein can be made active by applying light of a selected wavelength and can be made immediately inactive by applying light of a different selected wavelength, or can be allowed to become gradually inactive by removing light of said different selected wavelength. In embodiments, the protein can be made inactive by applying light of a selected wavelength and can be made immediately active by applying light of a different selected wavelength, or can be allowed to become gradually active by removing said light of a different selected wavelength. In embodiments, the fusion proteins hereof can be controlled to be substantially completely inactive or substantially completely inactive by the foregoing means (when high light activation ratios are achieved), or can be controlled to be relatively inactive or to be relative active (when low light activation ratios are achieved).

A "fusion site" defines the amino acid of the photoreceptor module that is linked to the specific amino acid of the output module of the fusion protein.

A "linker region" of fusion protein hereof is the α-helical protein region that includes a fusion site. The linker region of the fusion protein may be composed entirely of α-helical regions or partly of α-helical region. Linker regions hereof may be shortened or lengthened using amino acid sequence of the photoreceptor module or artificial sequence in order to cause or improve control of activity of NIRLAHPs by light.

A "plurality" as used herein means two or more.

Embodiments

Methods are provided herein for producing photoactive fusion proteins based on photoreceptor modules of bacteriophytochromes having a desired activity controllable by near-infrared (NIR) light, said methods comprising the steps:
a. identifying, based on biochemical information, candidate protein output domains that function as homodimers and can be activated by homodimerization;
b. using 3D structures or building 3D models to identify optimal fusion sites and peptide linkers for attaching the heterologous output modules to the bacteriophytochrome photoreceptor module;
c. producing a plurality of DNA molecules (a DNA library), each encoding a monomer of the homodimeric fusion protein that has at least one unique fusion site or linker sequence;
d. screening the DNA molecules for their ability to produce homodimeric photoactive fusion proteins capable of performing the desired activity in a test organism, wherein the screening is done by transforming the test organism designed to respond to the desired activity with the DNA library; allowing the expressed fusion proteins to spontaneously bind biliverdin IXα and form homodimers; applying light of selected wavelengths to the transformed organisms; and comparing the level of said desired activity of the expressed fusion proteins in the test organism in the dark and in the light;
e. optionally subjecting fusion proteins that have NIR light-activated activities identified by screening to random mutagenesis and subsequent screening (as described above) for mutant derivatives with improved qualities, e.g., low activity in the dark and high photoactivation ratio; and
f. purification, and spectral and biochemical characterization of fusion proteins produced by screening to assess their activity levels and photoactivation ratios in vitro.

Candidate output activity to be regulated by NIR light resides within a homodimeric protein. Desired output activity is revealed upon homodimerization, while monomeric output domains should have no or low, background, activity.

Analysis of existing 3D structures and structure modeling of proteins having a desired activity can be performed to identify suitable output modules. The N-terminal boundaries of the functional output domains are defined, and a distance between the N-terminal boundaries is estimated based either on 3D structures or models of 3D structures. This distance is compared to the distance between the C-termini of α-helices extending from the PHY domains of the bacteriophytochome photoreceptor module (PAS-GAF-PHY) homodimer that will be used for fusion. These distances need to be within several angstoms (Å) from each other. Should the distances deviate by more than approximately 10 Å, prior to designing fusion sites, adjustments are made by increasing or decreasing the length of α-helixes extending from the PHY domains of the bacteriophytochome photoreceptor module. Said adjustments will change the distance between the C-termini of α-helixes to better match (within several Å) the distance between the N-terminal boundaries of the functional homodimeric output domains. Structures of many proteins having desired activities, protein 3D structure modeling approaches and software are known to the art. Extension of α-helixes may rely on native sequence of the bacteriophytochrome protein or on artificial amino acid sequences known to form α-helixes. Should modification of the lengths of α-helixes extending from the PHY domains be insufficient for bringing the distances between said α-helixes and the N-terminal boundaries of the homodimeric output domains in the proximity of several Å, positions of the N-terminal boundaries can be adjusted, i.e., shortened or extended, provided that such adjustments preserve activity of the homodimeric output modules. Prior to constructing fusion proteins, activities of homodimeric output modules are verified in vitro.

Once the fusion site is chosen, a fusion encoding the chimeric protein is made and tested for desired activity and photoactivation ratio. Typically, a plurality of fusions (a DNA library) is made where the N-terminal position of the output domain is fixed, while the α-helical linkers extending from the PHY domain of the bacteriophytochrome photoreceptor module are made to differ from each other by a single amino acid. Once a fusion protein having the desired NIR light-activated or NIR light-inactivated activity is identified, it has been found that shortening or lengthening the α-helices extending from the PHY domain by one or two α-helical turns will form additional proteins that are also light-activated (or light-inactivated). An α-helical turn, approximately 3.6 amino acids, can be approximated by 3 and 4 amino acid extensions and deletions.

The bacteriophytochrome photoreceptor module that provides sensitivity to light in embodiments is a photoreceptor module from the *Rhodobacter sphaeroides* BphG1 protein comprising PAS-GAF-PHY domains. The photoreceptor module binds its chromophore, a biliverdin IXα, in vivo and in vitro due to intrinsic biliverdin ligase activity.

The output module can be selected from enzymes and other proteins that have a desired biological activity, e.g., enzymatic activity, or ability to bind DNA, RNA or other proteins. In embodiments, the output modules can include protein kinases, proteases (including caspases), nucleotidyl cyclases, nucleases (including recombinases), DNA-binding and RNA-binding protein modules, and others that are activated by homodimerization.

Some photoactive fusion proteins can be activated or their activity can be enhanced by the application of light of an activating wavelength. They can be inactivated, or their activity can be reduced by the absence of light or by the application of light of an inactivating wavelength. Some photoactive proteins can be active or show enhanced activity in the dark or reduced light, and be inactivated or show reduced activity when light of an inactivating wavelength is applied. The "absence of light" can mean the absence of all light (i.e., darkness), or can mean the absence of light in a selected wavelength range that causes a change in the conformation of the bacteriophytochrome photoreceptor module.

In embodiments, in which the fusion protein is in a stable active form (i.e., the output module is in a conformation such that it performs a desired activity when no NIR light is applied), when NIR light of a first wavelength is applied, the conformation of the output module changes and the output module immediately becomes inactive. In such embodiments, the inactive state is relatively unstable. When NIR light of a second wavelength is applied to the fusion protein, it immediately reverts to the stable, active form. If light of the second wavelength is not applied, then the fusion protein gradually reverts to its stable, active form.

In embodiments, in which the fusion protein has a stable inactive form, the opposite is true: the fusion protein is inactive until NIR light of a first wavelength is applied. Then it immediately becomes active. It can be immediately inactivated by application of NIR light of a second wavelength or it can be gradually inactivated by not applying NIR light of the second wavelength.

Thus, in embodiments the desired activity is increased by the application of NIR light of a selected wavelength. In embodiments the desired activity is decreased by the application of NIR light of a selected wavelength. In embodiments the desired activity is gradually decreased or gradually increased by ceasing to apply NIR light of a selected wavelength. In embodiments the desired activity is immediately increased or decreased by the application of NIR light of a selected wavelength. Suitable selected wavelengths are determined by the spectral properties of the bacteriophytochrome photoreceptor module and readily ascertained by those of ordinary skill in the art without undue experimentation.

It is to be understood that the terms "active" and "inactive" in the foregoing explanation are relative and include complete activity of the protein to complete inactivity of the protein (complete "on/off" modes) as well as relative activity or inactivity of the proteins, i.e., the fusion proteins can have high activation ratios, low activation ratios, or activation ratios between high and low. In embodiments the fusion proteins can be controlled by light to have high ratios of activity to inactivity or of inactivity to activity under the control of light of appropriate wavelengths. High ratios are defined herein as ratios of about 2:1 or greater, in embodiments, about 5:1 to about 10:1 or greater. Low ratios are less than about 2:1.

In embodiments, the fusion proteins to be screened can be produced in test organisms already having endogenous chromophore molecules that will bind with the fusion proteins as they are expressed.

In embodiments where no or insufficient chromophore molecules are endogenously available in the test organisms, in addition to producing DNA molecules encoding the designed fusion proteins and expressing them in test organisms, DNA encoding a heme oxygenase can also be expressed in the test organisms, e.g. *Rhodobacter sphaeroides* heme oxygenase BphO1 (RSP_4190) (Tarutina et al., 2006). The heme oxygenase degrades heme that is present in the test organisms to produce biliverdin IXα chromophore, which then binds to the expressed fusion proteins and make them photoactive. The DNA encoding the fusion proteins can be introduced into the test organisms on the same expression cassette as the DNA encoding heme oxygenase. Suitable expression cassettes comprising DNA for expression under control of appropriate regulatory elements such as promoters are known to the art.

Test organisms for use herein can be any organisms known to the art in which the level of the desired activity can be detected, including cultured organisms selected from the group consisting of *E. coli*, yeast, plant, or animal cells selected or modified so as to detectably exhibit the level of activity of the expressed fusion proteins under control of NIR light.

When using the fusion proteins produced by the present methods to treat living cells or organisms by controlling processes in these cells or organisms, there can be sufficient endogenous chromophores in the organisms to bind with the expressed fusion proteins, or if not, the organisms can be transformed with a heme oxygenase gene that will be expressed to produce heme oxygenase, which degrades heme that is present in the organisms to produce the chromophore molecules that will bind with the expressed fusion proteins in vivo.

In embodiments, additional fusion proteins controllable by NIR light can be produced by mutagenizing genes encoding "first-generation" NIRLAHPs to create fusion proteins that have lower background activities and higher photoactivation ratios. Mutagenesis was found to improve such protein parameters when applied to DNA encoding the α-helical region linking the PHY domain with the output domain, as well as when applied to the full-length gene encoding a fusion protein.

Thus, fusion proteins that are found to be controllable by NIR light can be the basis for designing additional candidate fusion proteins by mutagenesis and repeating the steps of producing DNA encoding the additional fusion proteins, transforming suitable organisms with this DNA, expressing the DNA, and screening the resultant fusion proteins for additional fusion proteins controllable by NIR light. DNA molecules encoding such additional designed fusion proteins are then made, expressed in test organisms, and screened for their levels of the desired activity.

To further enhance the photoactivation ratios of fusion proteins, the second generation fusion proteins generated by mutagenesis of the first-generation fusion proteins can be mutagenized further to create improved NIRLAHPs. DNA molecules encoding such further designed fusion proteins are then made, expressed in test organisms, and screened for their levels of the desired activity. The methods hereof comprise selecting or constructing a suitable organism for producing and screening the plurality of DNA molecules (DNA library) encoding NIR light-activated fusion proteins. Any suitable organism known to the art for expression of fusion proteins can be used, so long as the level of the desired activity of the proteins in the organism can be detected. In embodiments, the level of the desired activity can be directly monitored by means known to the art, e.g., by detecting the blue color of β-galactosidase when it is a marker for a protein produced as the desired activity of the fusion protein. In embodiments, the test organism can be modified as is known to the art to allow detecting of the desired activity of the fusion protein. For example, the test organism can be engineered to allow detection of the desired activity by mutagenesis to prevent it from producing a substance that it would normally produce, so that it can only produce this substance if it expresses an active fusion protein.

The photoactive fusion protein can have any activity known to the art. Typically the activity involves control of a process in vivo such as a metabolic process, signal transduction, cell apoptosis, cell proliferation, cell adhesion, or cell differentiation. In embodiments, the photoactive fusion protein is selected from the group consisting of a light-activated nucleotidyl cyclase, such as adenylyl cyclases or guanylyl cyclase, and a light-activated uncleavable procaspase-3.

NIR photoactive fusion proteins are also provided herein. Such proteins can be produced by the methods described above, or by methods analogous thereto that can be designed and carried out by those of ordinary skill in the art without undue experimentation.

Further provided herein are recombinant DNA molecules encoding the homodimeric fusion proteins described herein. Expression cassettes comprising such DNA molecules under control of appropriate regulatory elements are also provided.

Also provided herein are methods for controlling an in vivo process in a host, which is a living cell or organism. The method comprises:
a. introducing into the cell or organism a DNA sequence encoding a homodimeric fusion protein comprising a bacteriophytochrome photoreceptor module and a heterologous output module capable of modulating the desired process;
b. introducing into the cell or organism a DNA sequence encoding a heme oxygenase capable of producing biliverdin IXα, if the endogenous level of biliverdin IXα in the cell or organism is insufficient for photoactivation;
c. providing a source of heme (the substrate for heme oxygenase), if the host cell or organism does not contain sufficient endogenous levels of heme; or providing biliverdin IXα;
d. allowing the fusion protein and heme oxygenase, where applicable, to be expressed in the host; and
e. applying NIR light of a selected wavelength to the host or preventing NIR light of a selected wavelength from reaching the host; thereby modulating the process under control of NIR light.

The in vivo process can be selected from the group consisting of metabolic processes, signal transduction, cell apoptosis, cell proliferation, cell adhesion, and cell differentiation. The photoreceptor module can be as described above, e.g., that of *Rhodobacter sphaeroides* BphG1 protein.

Detailed Discussion

The engineering principles disclosed herein are applied to select and optimize NIR light-activated homodimeric proteins (NIRLAHPs). These proteins can be used to turn on (or turn off) desired activities in transgenic animals, plants or microbes.

Bacteriophytochromes can significantly expand the range of optogenetic applications: (i) They absorb light of the far-red/NIR spectrum (Rockwell et al., 2006, FIG. 1B), which penetrates animal tissues much deeper than visible light sensed by currently used photoreceptors (Cuberddu et al., 1999; Wan et al., 1981; Byrnes et al., 2005). (ii) NIR light is harmless; for example, it is currently used in human optical imaging and deep-tissue phototherapies (Fang et al., 2009; Desmet et al., 2006). (iii) The biliverdin chromophore of bacteriophytochromes is the first product of heme breakdown and thus is naturally produced by most animal cells (Rockwell et al., 2006). If insufficient, biliverdin (which is nontoxic in small doses) can be directly injected (Shu et al., 2009) or supplied by a bacterial heme oxygenase, (iv) Phytochromes can be instantly turned "off" (i.e., photoinactivated) by longer wavelength light (Rockwell et al., 2006); which provides for excellent temporal control, (v) Lastly, recently (far-red light absorbing) phytochrome-based fluorescent proteins have been expressed in mice and used for whole-body imaging, which proves that phytochromes expressed in deep tissues can be activated by external light sources in small mammals (Shu et al., 2009). In sum, NIR light-activated proteins can significantly broaden the range of optogenetic applications and allow researchers to use these approaches in the mammalian models of development and diseases as well as in other organisms.

Bacteriophytochromes function as homodimers. The light-induced conformational changes in the photosensory module of one monomer are presumed to rotate its output domain and bring it into proximity with the output domain of the second monomer, thus generating an active conformation of the homodimer. Natural bacteriophytochromes have different homodimeric outputs, e.g., His-kinases and diguanylyl cyclases.

This disclosure illustrates engineering of photoactivated versions of nucleotidyl cyclases and executioner caspase. Engineering principles for constructing NIR light-activated homodimeric proteins are provided. Since a large number of signaling proteins function as homodimers, NIR light-induced protein homodimerization can be used to control a variety of cellular functions including metabolic processes, signal transduction, cell apoptosis, differentiation, proliferation, transformation and adhesion.

This disclosure illustrates engineering of NIRLAHPs using the BphG1 protein from *R. sphaeroides*. However, numerous bacteriophytochromes are present in the genomes of microbes, primarily in bacteria. Because they likely undergo similar light-induced conformational changes to those that occur in BphG, these bacteriophytochromes can also be used as sources of photoreceptor modules for protein engineering.

Construction of photoactivated fusions starts with identification of output activities known to be activated by homodimerization. Subsequently, analysis of 3D structures (or structural models) of the photosensory module and homodimeric output module is undertaken. A fusion point for creating photoactivated chimeric proteins is based on using approximately the same distance (in three-dimensional space) between the C-termini of the α-helices extending from the PHY domains of the homodimeric photosensory modules as the distance between the N-termini of the homodimeric output modules. These distances are derived from 3D structures (X-ray and NMR) or structural models built based on 3D structures. The α-helices extending from the PHY domains can be shortened or extended to accommodate the N-termini of the output module. The fusions can occur at different boundaries of the output module; therefore, several fusion sites are tested to identify fusion proteins with optimal parameters, i.e., high photoactivation ratio (the ratio of protein activity in the light to that in the dark, also known as dynamic range) and low activity in the inactive state (which is the dark state for photoactivated proteins, or lit state in the photoinactivated proteins). Our analysis of an engineered NIRLAHP-adenylyl cyclases (where the output module is the adenylyl cyclase domain of the CyaB1 protein from *Nostoc* sp.) suggests that the light-induced conformational changes in the photosensory domain of a bacteriophytochrome monomer result in a movement, that may involve rotation, of its output domain that brings it in proximity with the output domain of the second monomer, thus generating an active homodimer.

The relative positions of the output domain monomers depend on the phase of the α-helices that link the PHY domains of the photosensory module to the output domains. The output domains that are linked on the same side of the α-helices display similar light responsiveness. For example, several light-activated fusion proteins have been obtained that differ from each other by multiples of 3 or 4 residues, which corresponds to one, two or more α-helical turns, where one α-helical turn is approximately 3.6 amino acid residues. The torque generated by the presumed rotation of the photosensory module following photon absorption is believed to change mutual arrangement (possibly via rotation) of the output domains. For transfer of the torque to the output domains, unstructured elements (e.g., loops) preceding the more rigidly structured elements of the output domains should be minimized.

Once a first-generation NIRLAHP is obtained, its photoactivation ratio can be improved via mutagenesis (e.g., via error-prone PCR mutagenesis using the whole fusion protein as a template at the rate of several mutations per gene, or via integration of degenerate synthetic DNA sequences).

NIRLAHPs possessing lower dark activities and higher photoactivation ratios, compared to the first-generation NIRLAHPs, can be identified following the same mutagenesis and screening procedures.

Selection and/or screening for the first-generation NIRLAHP of its class as well as identification of mutants with maximal photoactivation ratios can be achieved by using specifically designed microbial or animal cells. For example, screening for a light-activated adenylyl cyclase is done in the E. coli mutant impaired in the cya gene that encodes a native adenylyl cyclase.

Cyclic nucleotides are universal second messengers that control various important biological processes. However, precise roles of cAMP and cGMP in many physiological processes and diseases remain unknown. A number of drugs for chronic obstructive pulmonary disease, bone marrow transplant rejection, and cancer increase cellular cAMP, which in turn decreases inflammation (reviewed in Serezani et al., 2008). Some of the primary signals inducing cAMP synthesis in cells include epinephrine, norepinephrine, histamine, serotonin, and certain prostaglandins (Landry et al., 2006). The photoactivated adenylyl cyclase allows understanding of signaling pathways with higher precision than that provided by the use of hormones. Blue-light-activated adenylyl cyclase from *Euglena gracilis* (Iseki et al., 2002) and *Beggiatoa* sp. (Ryu et al., 2010; Stierl et al., 2011) can be applied to study various biological processes in cell cultures and animals transparent to light, e.g. zebrafish. The NIR light version of adenylyl cyclases allows researchers to study cAMP-signaling in both transparent model organisms and, importantly, organisms that are non-transparent to visible light, e.g. red-blooded animals.

The near-infrared light version of guanylyl cyclase can be made by site-directed mutagenesis of as few as 2-3 amino acid residues in the adenylyl cyclase (ACyc) domain as known in the art (Ryu et al., 2010)

Figure 2:
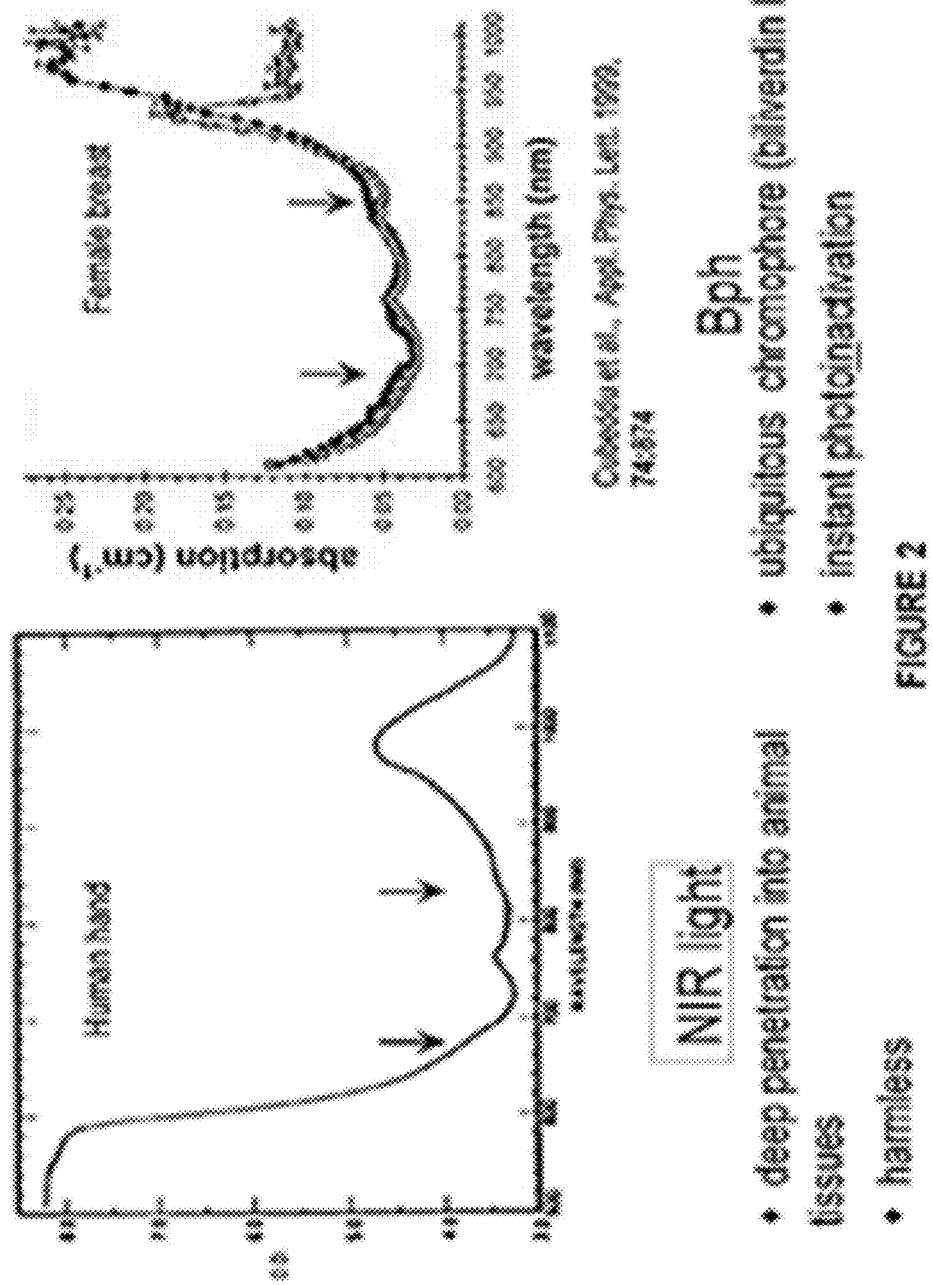
FIG. 2 illustrates major advantages of biliverdin IXα containing bacteriophytochromes as photoreceptor modules for engineering light-activated proteins for use in mammals. These advantages include deep penetration of NIR into mammalian tissue, lack of toxicity, ubiquity of biliverdin IXα in mammalian tissue (as natural product of heme turnover) and instant photoinactivation. Left top panel: absorbance of light passing through flesh of a human hand. Right top panel: the absorbance of human breast tissue at different wavelengths. Arrows approximately delimit the range of the spectrum with low light absorption by human tissues, which provide for deeper light penetration.
Figure 3:
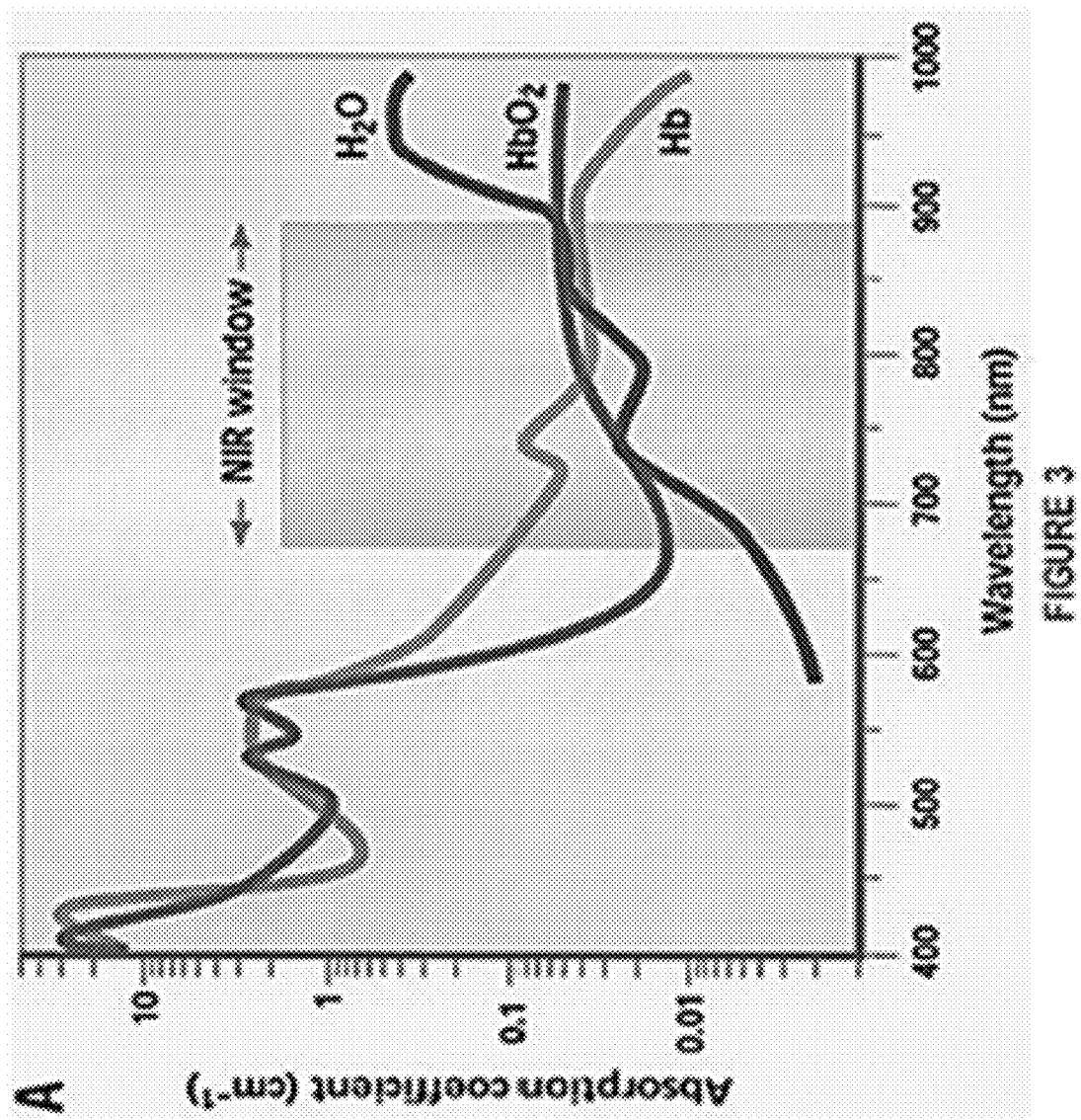
FIG. 3 shows the "NIR window" from about 670 nm to about 890 nm, where cumulative absorption by three major light-absorbing components of flesh in red-blooded animals, deoxyhemoglobin (Hb), oxyhemoglobin ($HbO_2$) and water ($H_2O$), is lowest (Weissleder, 2001). The NIR window identifies the range of wavelengths that can be used for deepest penetration through mammalian tissues. Bacteriophytochrome absorption peaks fall into the NIR window.

Photoactivated caspases, are another biological tool disclosed herein. They allow researchers to conduct targeted cell/tissue killing in vivo using NIR light, and are applicable in many areas of biology and medicine, particularly in tumor biology, immunology and developmental biology. Currently-available approaches that target cells for killing, e.g., laser ablation, and chromophore-assisted light-inactivation with chemical or genetically encoded photosensitizers (Jacobson et al., 2002; Bulina et al., 2006), are harsher (i.e., damage nearby cells/tissues), less precise and/or poorly applicable to mammalian models. A photoactivated caspase, whose gene can be delivered in tumors (e.g., by recombinant viruses, bacteria or nanoparticles), can be used as a readily controllable cancer gene therapy. It can be used in isolation or in combination with already-existing cancer treatments (e.g., cytotoxic drugs). A blue-light activated executioner caspase-7 has recently been engineered and shown to efficiently kill cells in cell culture in response to blue light (Mills et al., 2012). However, the utility of blue-light activated caspase, as well as other blue-light activated proteins is limited in red-blooded animals because of low light penetration through animal tissues (FIGS. 2, 3). Therefore, a NIR-activated caspase represents a transformative improvement that enables its use in animal models of disease and development.

Engineering and Optimizing Near-Infrared Light-Activated Nucleotidyl Cyclases.Cyclic nucleotides are universal second messengers that control a variety of processes including cell growth and differentiation, blood glucose levels, cardiac contractile function, learning, memory, and other processes known to the art. The ability to activate cAMP and/or cGMP synthesis in desired cells at specific development/disease times is used to provide new and important mechanistic insights into cyclic nucleotide signaling.

Figure 7:
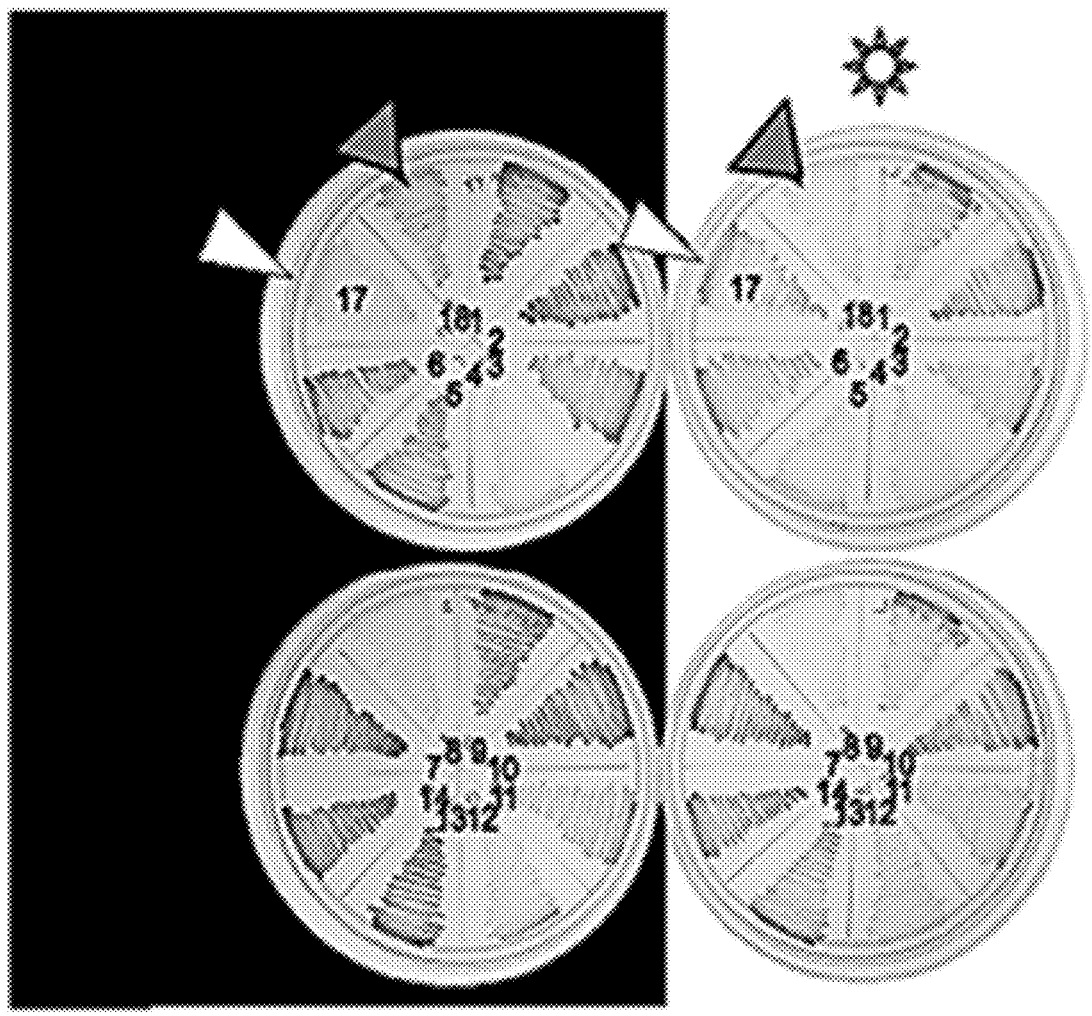
FIG. 7 illustrates XGal indicator plates containing representative *E. coli* clones, each having a gene encoding a different (numbered) fusion adenylyl cyclase protein construct, grown either in the dark (left panel) or in the light (right panel). Blue color indicates how each clone responds to light. The white arrowhead points to the clone containing a light-activated adenylyl cyclase having the sequence: MAQRTRAELE RKEVT (SEQ ID NO:6): the black arrowhead points to one of the light-inactivated adenylyl cyclases having the sequence MAQRTRAELA RLRHYDERKE VT (SEQ ID NO:1).
Figure 8:
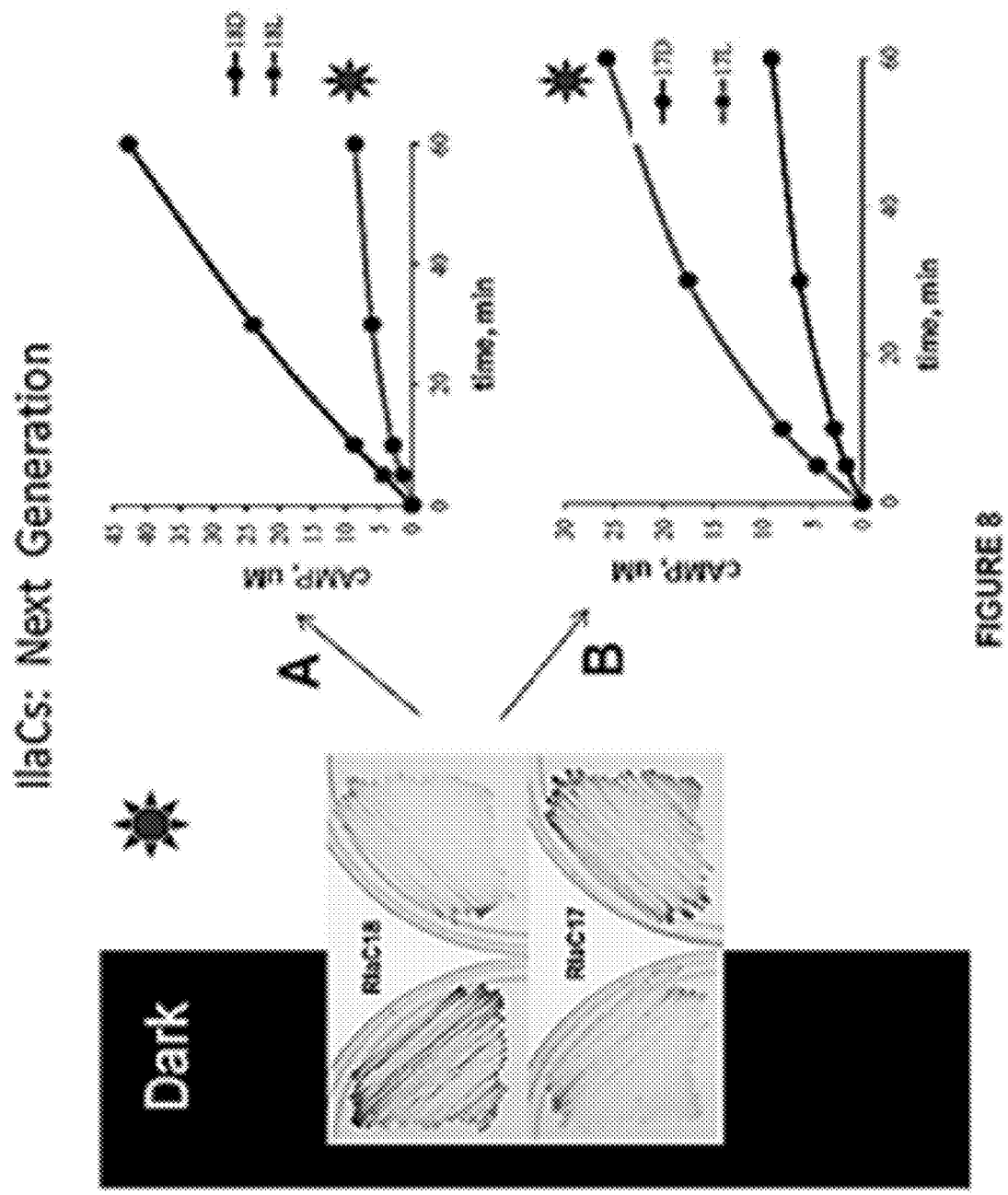
FIG. 8 shows images of *E. coli* clones containing selected light-activated (SEQ ID NO:6, MAQRTERKEV T (SEQ ID NO:10) and light-inactivated (SEQ ID NO:1) fusion adenylyl cyclase proteins grown in the dark and light, along with adenylyl cyclase activities of the purified proteins measured under light and dark conditions in vitro.
Figure 8:
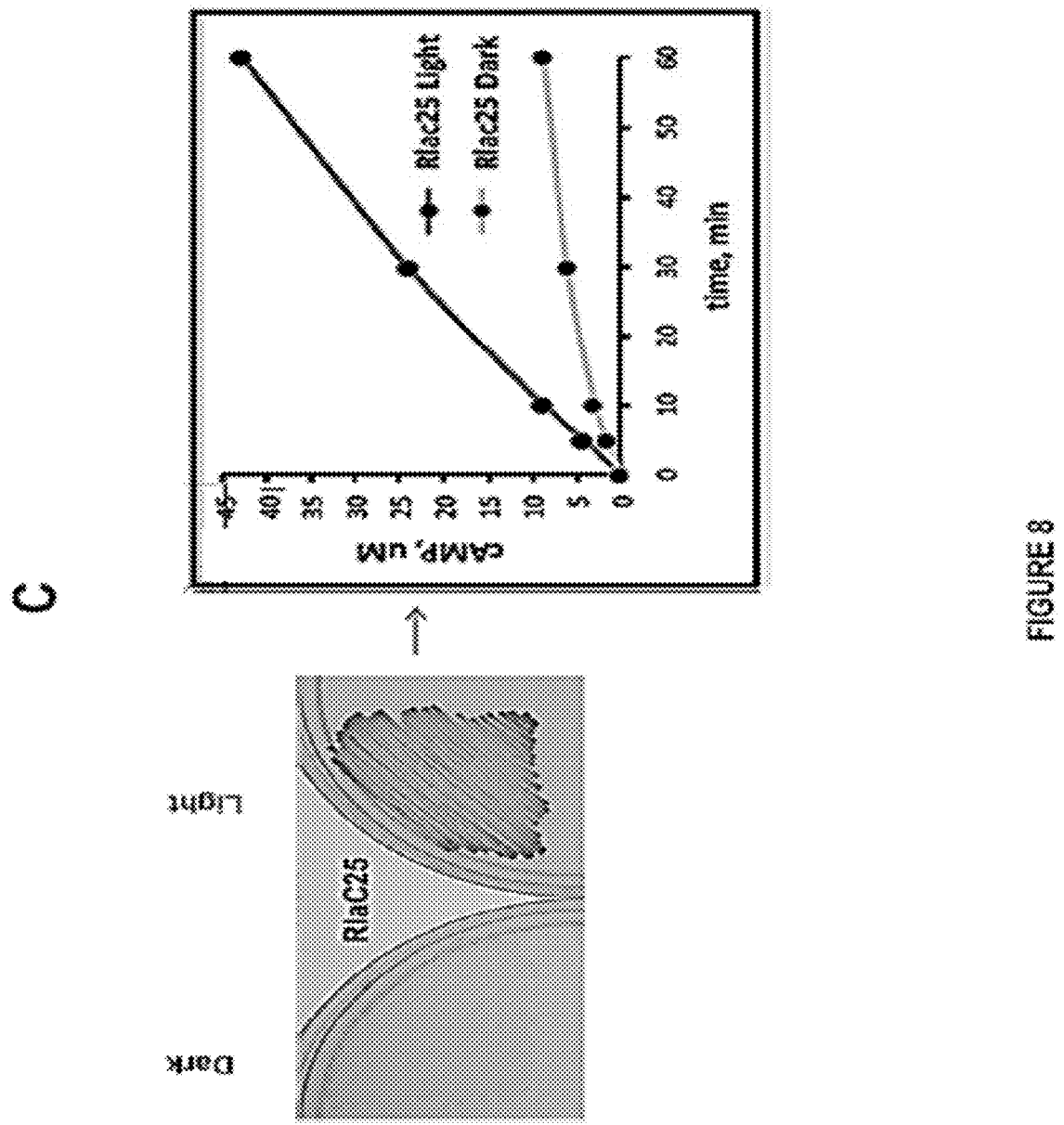
Figure 9:
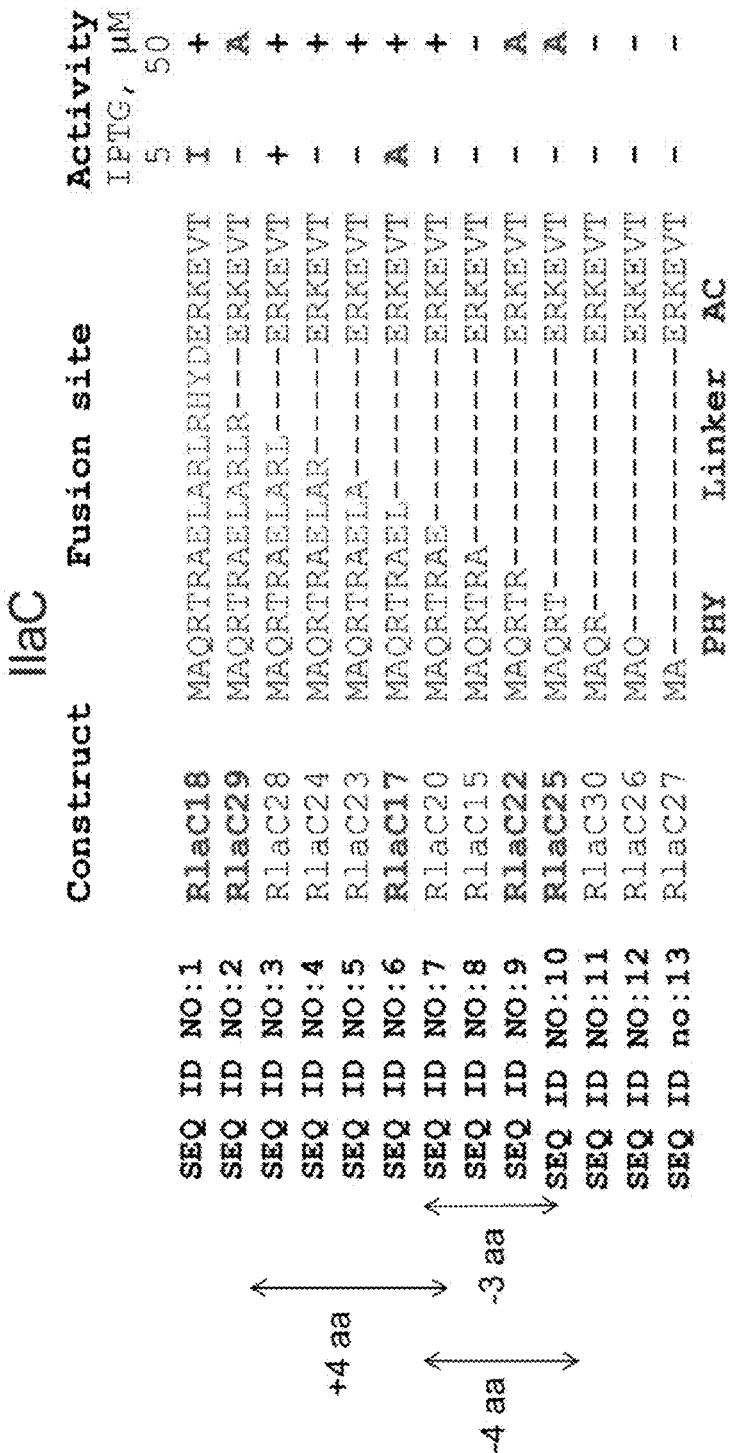
FIG. 9 provides protein sequences near fusion points of selected engineered adenylyl cyclase fusions between the photoreceptor module of BphG and adenylyl cyclase (ACyc domain) of CyaB1. Photoresponses in *E. coil* of the fusion proteins were recorded at two levels of expression of the chimeric proteins: low (5 µM isopropyl-beta-D-thiogalactopyranoside, IPTG) and high (50 µM IPTG). β-galactosidase expression (judged by the intensity of blue color) is dependent on intracellular cAMP levels. A: light-activated (higher β-galactosidase expression in the light versus dark); I: light-inactivated (higher β-galactosidase expression in the dark versus light);+:light-independent activity; –: no activity (in the dark or light). It is emphasized that protein fusions containing approximately one helical turn (+/–3-4 amino acids, aa) longer or shorter α-helical sequences had the same type of light-responsiveness, e.g., light-activated SEQ ID NO:6; MAQRTRAELA RLRERKEVT (SEQ ID NO:2) (SEQ ID NO:6+4 aa); SEQ ID NO:10( SEQ ID NO:6- 4 aa); and MAQRTRERKE VT SEQ ID NO:9 (SEQ ID NO:6- 3 aa).

As shown herein, bacteriophytochrome photosensory modules Were engineered to activate heterologous outputs. In an embodiment hereof, to construct NIR light-activated nucleotidyl cyclases, the diguanylyl cyclase GGDEF domain from the photoactivated diguanylyl cyclase, designated BphG, from *Rhodobacter sphaeroides* was replaced with a distantly related adenylyl cyclase (ACyc) domain from *Nostoc* sp. protein CyaB1 resulting in the production of photoactivated adenylyl cyclase, designated RlaC (FIG. 7-9). The first-generation adenylyl cyclases were mutagenized to identify variant enzymes with the highest photoactivation ratio and lowest activities in the dark. Optimized adenylyl cyclase is used as a template to engineer a NIR light-activated guanylyl cyclase as described by Ryu et al. (2010).

Engineering and Optimizing Near-Infrared Light-Activated Executioner Caspases.Executioner (effector) caspases are terminal cysteine proteases initiating apoptosis (programmed cell death). An engineered photoactivated executioner caspase is useful to induce apoptosis in desired cells or tissues of recombinant animals expressing it in specific tissues. A gene for a photoactivated caspase can also be delivered to tumors and used in noninvasive cancer gene therapy. In an embodiment hereof, a derivative of the executioner caspase, procaspase-3, which is activated by homodimerization, is engineered using principles developed from engineering and optimizing near-infrared light-activated nucleotidyl cyclases to construct a near-infrared light-activated caspase. All engineered enzymes are biochemically characterized in vitro. Prioritized constructs are moved into *Drosophila melanogaster*, mice and other organisms.

The following description of various specific embodiments is exemplary in nature and is in no way intended to limit the scope of the claims hereof. In embodiments, art-known equivalents of exemplified components, materials and method steps can be substituted for those specifically described herein and these embodiments are considered to fall within the scope of the claims. Embodiments including less than all the components, materials and method steps of embodiments specifically described herein are also, considered to be encompassed within this disclosure.

Figure 4:
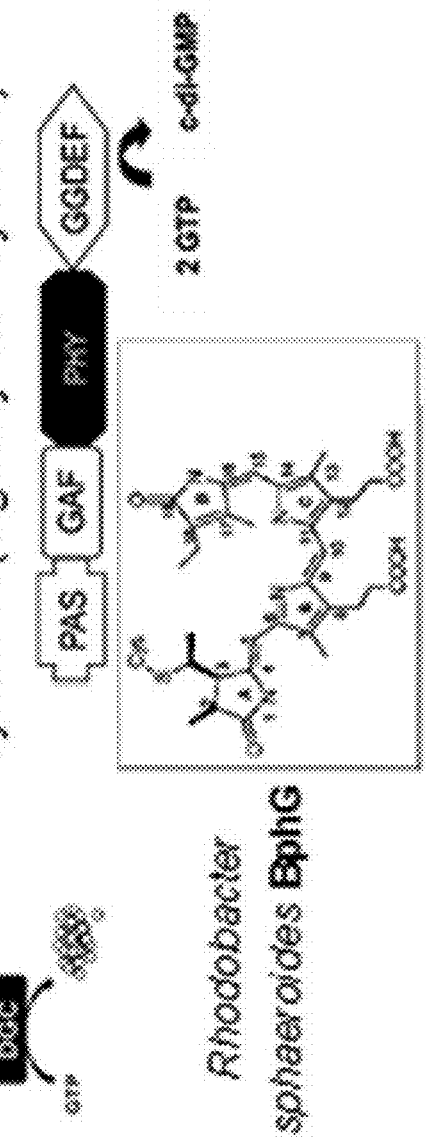
FIG. 4 illustrates protein domain architecture (top panel) as well as spectral and enzymatic properties (bottom panel) of the BphG protein used for protein engineering. Top panel, *R. sphaeroides* BphG (PAS-GAF-PHY-GGDEF), a derivative of BphG1 (PAS-GAF-PHY-GGDEF-EAL) lacking the EAL domain (Tarutina et al., 2006). BphG converts two guanosine triphosphate (GTP) molecules into cyclic dimeric GMP (c-di-GMP) by means of a diguanylate cyclase activity of the GGDEF domain (Ryjenkov et al., 2005). Bottom panel, left: spectral properties of BphG (same as in FIG. 2). Bottom panel, right: synthesis of c-di-GMP by *R. sphaeroides* BphG in vitro, in the dark (grey line) and in the light (black line). BphG has an approximately 10-fold photoactivation ratio (relative activity in the light divided by relative activity in the dark).
Figure 4:
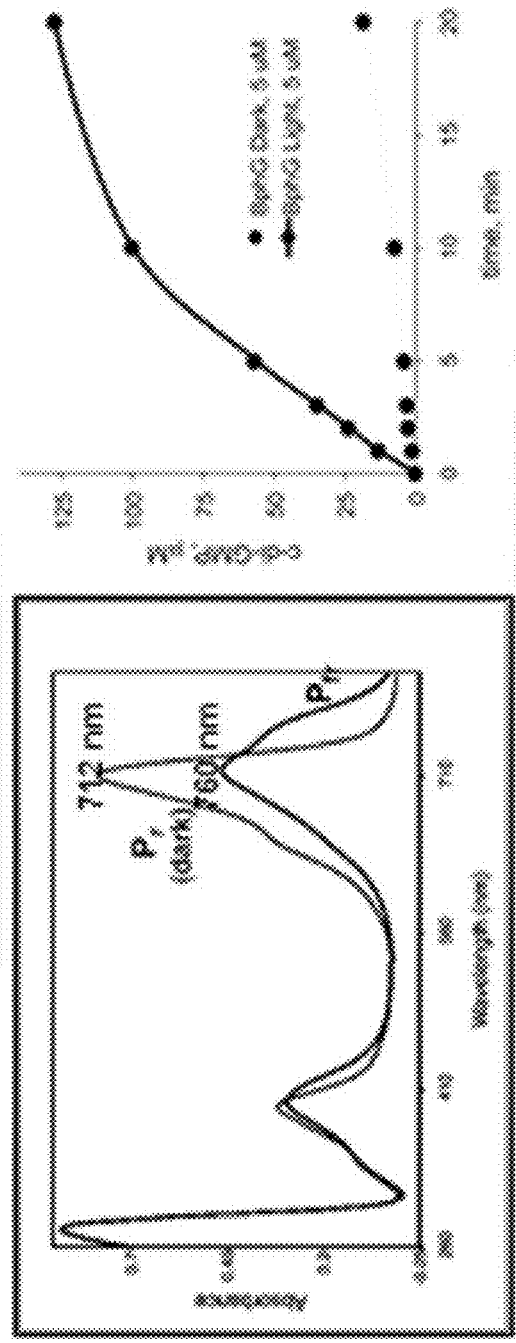

FIG. 1 (top panel) depicts six major types of photoreceptors (molecules that organisms use to detect light): opsins, which are human retinal photosensors and rhodopsins of various microbes; cryptochromes, which are blue light-sensitive flavoproteins found in plants, animals and microbes; photoactive yellow protein (PYP) photosensors, which are found in certain bacteria; photoreceptors of blue-light using flavin adenine dinucleotide (BLUF) and Light, Oxygen, or Voltage sensing (LOV) types, which are plant and bacterial photoreceptors; and phytochromes, which are used by plants and microbes and are sensitive to light in the red-to-NIR region. Work done to illustrate the presently-claimed methods was done using a bacteriophytochrome, a subclass of phytochromes that covalently bind biliverdin IXα as a chromophore (a molecule bound to the photoreceptor protein that detect slight and cause a conformational change in the protein when hit with a photon of light). The bacteriophytochrome (Bph) used herein was *Rhodobacter sphaeroides* BphG, which converts two guanosine triphosphate (GTP) molecules into cyclic dimeric guanosine monophosphate, c-di-GMP. As shown in the lower left panel of FIG. 1, the dark form of BphG, has a protein conformation designated Pr, which is present in the dark or absence of 650-715 nm light. When light having a wavelength between about 650 and about 715 nanometers strikes the chromophore, it causes a rearrangement of the molecule to an isomeric form designated as far-red, Pfr, conformation, in which the double bond (between C15 and C16) shifts from the cis to trans conformation. The protein absorbs light maximally at 712 nm resulting in the red-shifted, Pfr, form, whose diguanylyl cyclase activity is approximately 10-fold higher compared to the activity of the Pr form, as shown in FIG. 4. The chromophore of the bacteriophytochrome has the chemical structure depicted in the lower right panel of FIG. 1.

Once formed upon irradiation, the Pfr form of BphG is fairly stable. In the dark it spontaneously converts to the Pr form in approximately 45 min (Tarutina et sl., 2006). If light of about 760 nm is applied, the Pfr form is converted to the Pr (dark) instantly. This reversible photoconversion feature is a unique, to phytochromes.

The present methods are especially useful for application in humans and other mammals because mammalian flesh is relatively transparent to far-red/NIR light. As shown in FIG. 2, left panel the absorption of light by a human hand decreases as the wavelength of the light changes from blue to far-red and NIR light, being at its lowest between about 680 to about 890 nm, in the so-called "NIR window" (FIG. 3). FIG. 2, right panel shows absorption of light in female breast tissue, again being minimal in the NIR window. The light in the NIR window can penetrate deeply into the body (many centimeters). The light in the NIR window is harmless because there are no chromophores in animals that absorb in the NIR window.

The main advantages of bacteriophytochromes in use in optogenetics are that their chromophore, biliverdin IXα, is made in mammals, where, as indicated in FIG. 2, it is produced as a natural breakdown product of heme. For use of the chimeric proteins hereof in mammals, there is no need for a step of administering the chromophore separately. Bacteriophytochromes can be instantly photoinactivated, e.g., by applying light of 750-780 nm for BphG. This provides for superior, compared to other photoreceptor types, temporal regulation of output activities of chimeric bacteriophytochromes.

In embodiments when using the fusion proteins hereof for treating an organism, the organism will produce sufficient chromophore molecules for effective use of the NIR-light-controlled fusion protein. However, if biliverdin Ixα is insufficient in a particular tissue or animal model, it can be administered externally (it is nontoxic to animals at low doses), or it can be synthesized by heme oxygenase that can be delivered as a gene on the same gene delivery platform as the chimeric bacteriophytochrome.

FIG. 3 shows the "NIR window" from about 670 nm to about 890 nm, where cumulative absorption by three major light-absorbing components of flesh in red-blooded animals, deoxyhemoglobin (Hb), oxyhemoglobin (HbO$_2$) and water (H$_2$O), is lowest (Weissleder, 2001). The "NIR window" identifies the range of wavelengths that can be used for deepest penetrating through mammalian tissues. Bacteriophytochrome absorption peaks fall into the "NIR window".

FIG. 4 illustrates protein domain architecture (top panel) as well as spectral and enzymatic properties (bottom panel) of the BphG protein used for protein engineering. Top panel: *R. sphaeroides* BphG (PAS-GAF-PHY-GGDEF) is a derivative of BphG1 (PAS-GAF-PHY-GGDEF-EAL) lacking the EAL domain (Tarutina et al., 2006). BphG converts two guanosine triphosphate (GTP) molecules into cyclic dimeric GMP (c-di-GMP) by means of a diguanylate cyclase activity of the GGDEF domain (Ryjenkov et al., 2005). Bottom panel, left: Spectral properties of BphG (same as in FIG. 2). Bottom panel, right: Synthesis of c-di-GMP by *R. sphaeroides* in vitro, in the dark (grey line) and in the light (black line);

FIG. 5A is a schematic depiction of the *R. sphaeroides* BphG protein comprising the photoreceptor (PAS-GAF-PHY) and output (GGDEF) modules. The BphG protein is depicted as a parallel homodimer. FIG. 5B is a 3D model of the BphG protein based on the 3D structure 3c2w for the photoreceptor module and 3icl for the output domain (3D structures from Protein Data Bank, PDB, rcsb.org/pdb). The dashed line represents approximate position in the α-helices extending from the photoreceptor domain for fusion with a heterologous homodimeric output module. An arrow indicates rotation of an output domain as a potential outcome of light-induced conformational changes in BphG. FIG. 5C depicts a 3D model of the homodimeric adenylyl cyclase domains of protein CyaB1 from *Nostoc* sp. (modeled based upon the PDB structure 1wc5). The output module of *R. sphaeroides* BphG, the diguanylyl cyclase GGDEF domain was replaced with a distantly related adenylyl cyclase (ACyc) domain from *Nostoc* sp. CyaB1 resulting in the photoactivated adenylyl cyclase. FIG. 5D is a schematic representation of the protein domain architecture (GAF-PAS-ACyc) of *Nostoc* sp. CyaB1 depicted as a homodimer.

Figure 6:
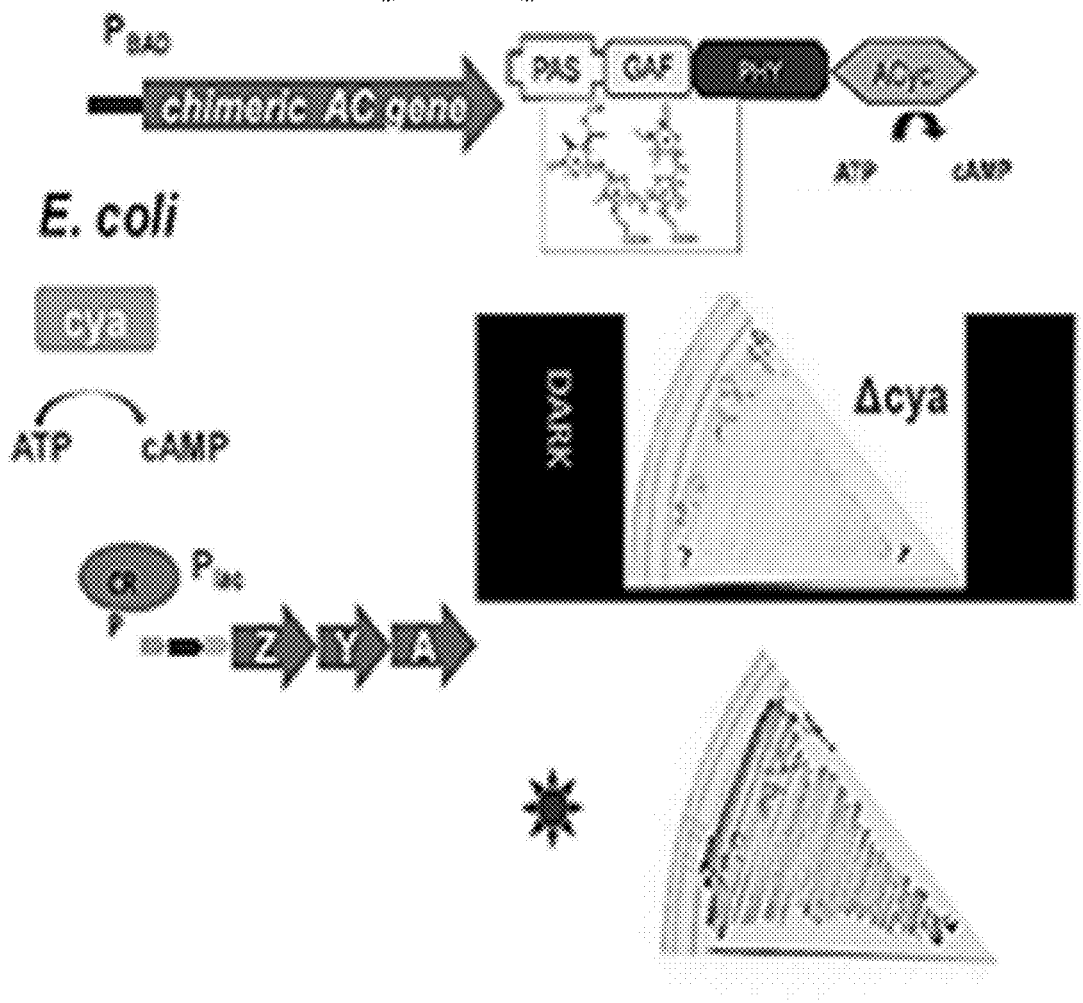
FIG. 6 illustrates the use of *E. coli* as a test organism to screen a DNA library of fusion protein constructs for adenylyl cyclase activity. A library of fusion proteins encoded by the "chimeric AC (adenylyl cyclase) genes" is expressed (e.g., from a $P_{BAD}$ promoter) in the *E. coli* strain having a cya gene deletion, which does not naturally produce cAMP. If the fusion protein generates cAMP, it enables expression of the (CRP-cAMP)-dependent lacZYA operon, which results in blue colonies on XGal indicator plates. In the absence of cAMP, the colonies are colorless. By comparing the color of colonies grown in the light (650-nm LED panel) and in the dark, one can identify light-activated and light-inactivated versions of adenylyl cyclases. The colonies appearing blue in the light and colorless (or less blue colored) in the dark contain candidate light-activated adenylyl cyclases. The colonies appearing colorless in the light and blue in the dark contain candidate light-inactivated adenylyl cyclases.

FIG. 6 illustrates the use of *E. coli* as a test organism to screen a library of fusion protein constructs for adenylyl cyclase activity. A library of fusion proteins encoded by the "chimeric AC (adenylyl cyclase) genes" is expressed (from a P$_{BAD}$ promoter) in the *E. coli* strain having a cya gene deletion, which does not naturally produce cAMP. If the fusion protein generates cAMP, it enables expression of the (CRP-cAMP-dependent) lacZYA operon, which results in blue colonies on XGal indicator plates. In the absence of cAMP, the colonies are colorless. By comparing the color of colonies grown in the light (650-nm LED panel) and in the dark, one can identify light-activated and light-inactivated versions of adenylyl cyclases. The colonies appearing blue in the light and colorless (or less blue colored) in the dark contain candidate light-activated adenylyl cyclases.

FIG. 7 illustrates XGal indicator plates containing representative *E. coli* clones, each having a gene encoding a different (numbered) fusion adenylyl cyclase protein construct, grown either in the dark (left panel) or in the light (right panel). Blue color indicates how each clone responds to light. The white arrowhead points to the clone containing a light-activated adenylyl cyclase [(#17)] (SEQ ID NO:6); the black arrowhead points to one of the light-inactivated adenylyl cyclases [(#18)] SEQ ID NO:1).

FIG. 8 shows images of *E. coil* clones containing selected light-activated [(#17 ,#25)] SEQ ID NQ:6, SEQ ID NO:10) and light-inactivated [(#18)] SEQ ID NO:1fusion adenylyl cyclase proteins grown in the dark and light, along with adenylyl cyclase activities measured using purified proteins under light and dark conditions.

FIG. 9 provides protein sequences near fusion points of selected engineered adenylyl cyclase fusions between the photoreceptor module of BphG and adenylyl cyclase (ACyc domain) of CyaB1. Photoresponses in *E. coli* of the fusion proteins were expressed at two levels of expression: low (5 µM isopropyl-beta-D-thiogalactopyranoside, (IPTG)) and high (50 µM IPTG). β-galactosidase expression (judged by the intensity of blue color) is dependent on intracellular cAMP levels. A. light-activated (higher β-galactosidase expression in the light versus dark); I, light-inactivated (higher β-galactosidase expression in the dark versus light); +, light-independent activity; −. no activity (in the dark or light). It is emphasized that protein fusions containing approximately one helical turn (+/−3-4 amino acids, aa) longer or shorter linkers had the same type of light-responsiveness, e.g. light-activated [#17] SEQ ID NO:6; [#29] SEQ ID NO:2([#17] SEQ ID NO:6 +4 aa); [#25] SEQ ID NO:10 ([#17] SEQ ID NO: 6+4aa); [#22] SEQ ID NO:9 ([#17] SEQ ID NO:6−3aa).

Figure 10:
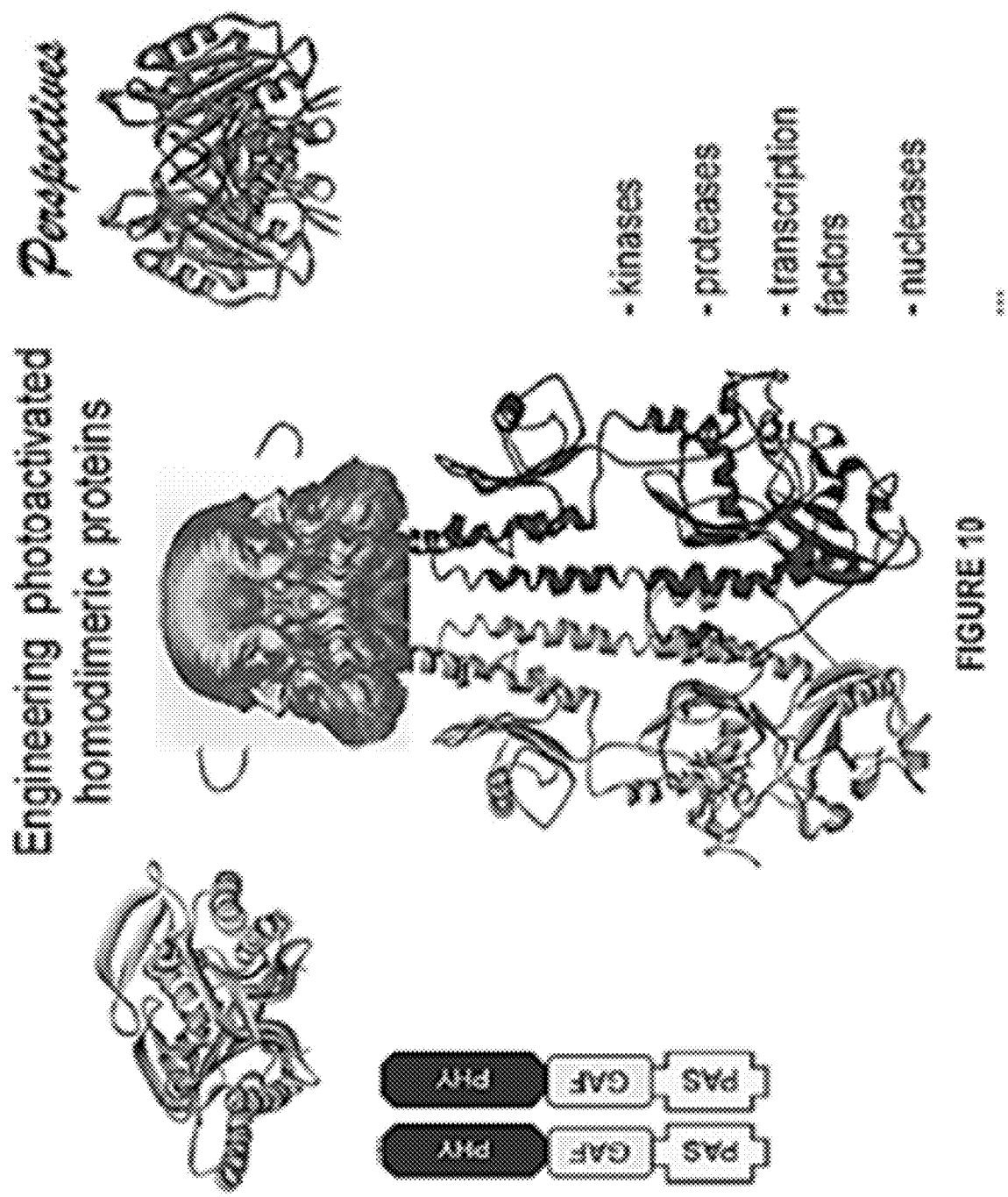
FIG. 10 illustrates an overview of principles elucidated herein. The photosensory module of a bacteriophytochrome is shown schematically in the lower left with a modeled heterologous active module shown above. In the center of the Figure, a modeled photosensory module is shown with the active module symbolized by a "homodimeric head". On the right, a generic modeled active module is illustrated above a list of examples of modules that can be used to engineer NIRLAHPs, e.g., kinases, proteases, transcription factors, nucleases, etc.

FIG. 10 illustrates an overview of principles elucidated herein. The photosensory module of a bacteriophytochrome is shown schematically in the lower left with a modeled heterologous active module shown above. In the center of the figure, a modeled photosensory module is shown with the active module symbolized by a "homodimeric head." On the right, a generic modeled active module is illustrated above a list of examples of modules that can be used to engineer NIRLAHPs, e.g., kinases, proteases, transcription factors, nucleases, etc.

To make a chimeric (fusion) protein hereof, one skilled in the art applying the principles taught herein can (1) pick a protein having an activity desired to be controlled by NIR light, that is active in a homodimeric form as two fused monomers, to supply the output module of the fusion protein that is capable of performing the desired activity; (2): provide a photosensory module comprising a bacteriophytochrome, such as that of the BphG protein of *Rhodobacter sphaeroides*; (3) determine possible fusion sites of the output module and receptor module by matching distances between fusion sites on the output module and the receptor module by lengthening and/or shortening the α-helix linkers of the output and/or photoreceptor module until their fusion sites correspond in space; (4) screen the constructs for light and dark activity; (5) upon identifying active constructs, find additional active constructs by making constructs with α-helical linkers 3-4 amino acids longer or shorter than those of the identified active constructs and screening them for activity; (6) further optimize the performance of the constructs by mutagenesis of either or both of the photosensory and active modules to find fusions that perform better, i.e., low activity in the dark and high activity in the light, or vice versa.

EXAMPLES

The near-infrared light-activated diguanylyl cyclase from *R. sphaeroides*, designated BphG, converts two GTP molecules into cyclic dimeric GMP (c-di-GMP) (Tarutina et al., 2006). The dark. Pr, form of BphG absorbs maximally at 712 nm resulting in the red-shifted, Pfr, form (FIG. 4, lower left panel), whose diguanylyl cyclase activity is approximately 10-fold higher compared to the activity of the Pr form (FIG. 4, right panel). To our knowledge, the photoactivation ratio in BphG is the highest among bacteriophytochromes for which such a ratio was measured. This makes BphG particularly attractive for protein engineering. The Pfr form of BphG can be brought back to the ground (dark, Pr) state by irradiation at 750-780 nm (maximum 760 nm, FIG. 4, left panel), which instantly turns the diguanylyl cyclase activity off (Tarutina et al., 2006).

Figure 5:
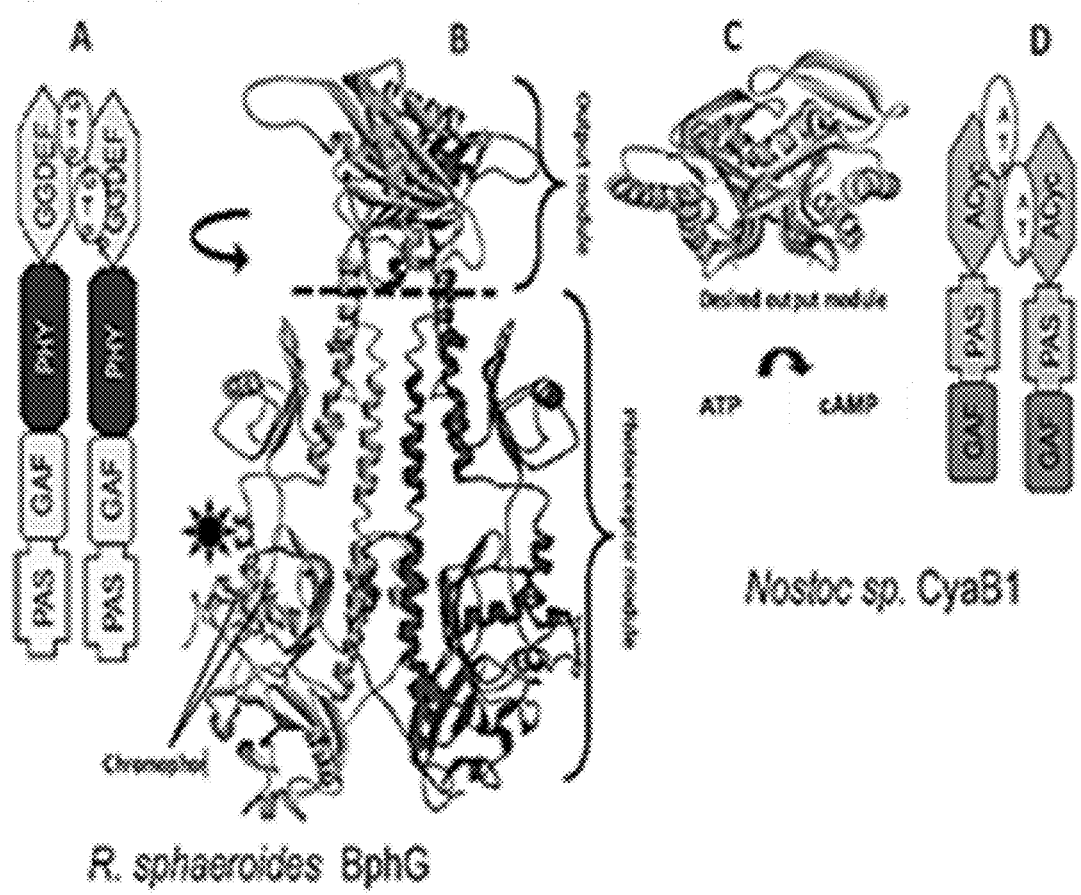
FIG. 5A is a schematic depiction of the *R. sphaeroides* BphG protein comprising the photoreceptor (PAS-GAF-PHY) and output (GGDEF) modules. The BphG protein is depicted as a parallel homodimer.
FIG. 5B is a 3D model of the BphG protein based on the 3D structure 3c2w for the photoreceptor module and 3ic1 for the output domain (3D structures from Protein Data Bank (PDB), rcsb.org/pdb). The dashed line represents the approximate position within the α-helices (extending from the photoreceptor PHY domain) for fusion with a heterologous homodimeric output module. An arrow indicates rotation of an output domain as a potential outcome of light-induced conformational changes in BphG.
FIG. 5G depicts a 3D model of the homodimeric adenylyl cyclase domains of protein CyaB1 from *Nostoc* sp. (modeled based upon the PDB structure 1wc5, the protein with the highest sequence identity to CyaB1). The output module of *R. sphaeroides* BphG, the diguanylyl cyclase GGDEF domain, was replaced with a distantly related adenylyl cyclase (ACyc) domain from *Nostoc* sp. CyaB1 resulting in the photoactivated adenylyl cyclase.
FIG. 5D is a schematic representation of the protein domain architecture (GAF-PAS-ACyc) of *Nostoc* sp. CyaB1 depicted as a homodimer.

Conformational changes following photon absorption are expected to result in the rotation or other movement type in the photosensory module that is transmitted as torque through the α-helixes extending from the PHY domain of the photoreceptor to the output domain of the photoactivated monomer (FIG. 5B). This motion brings two output domains into an active homodimeric state (Yang et al., 2008; 2009). The photosensory module of bacteriophytochromes is capable of activating diverse homodimeric outputs. A two-tiered test of this model was performed. First, we replaced the diguanylyl cyclase GGDEF domain of BphG with a distantly related (~15% sequence identity) bacterial adenylyl cyclase: (ACyc) domain such that the structural relatedness (Pei and Grishin, 2001; Sinha and Sprang, 2006) would increase the chance of a successful domain swap as shown in FIG. 5. Next, we focused on optimizing performance of the photoactivated adenylyl cyclase and constructing a near-infrared light-activated guanylyl cyclase using engineering principles developed in this work to construct a photoactivated homodimeric caspase-3 whose structure is completely unrelated to GGDEF.

Example 1

Engineering and Optimizing Near-Infrared Light-Activated Adenylyl and Guanylyl Cyclases For selecting photoactivated adenylyl cyclases, we constructed a cya deletion mutant, *E. coli* BL21 cya. This strain is devoid of its native adenylyl cyclase (cya mutation) and, therefore, produces white colonies on XGal indicator plates. Plasmid pBphO, expressing the *R. sphaeroides* heme oxygenase, bphO1, which makes biliverdin IXα is introduced in this strain.

We constructed a structural model of the BphG homodimer based upon the most closely related protein structures available in the Protein Data Bank (PDB), i.e., 3c2w for the (PAS-GAF-PHY) photosensory module and 3icl for the GGDEF domain (FIG. 5B) (Kuzin et al., 2009). As a source of the ACyc domain we chose an extensively biochemically characterized cyanobacterial adenylyl cyclase CyaB1. An important consideration for choosing CyaB1 was that its ACyc domains are known to spontaneously dimerize and form homodimers with significant cyclase activity (even in the absence of the regulatory domains) (Bruder et al., 2005). Therefore, once the two ACyc domains are brought in proximity, they were expected to form an active enzyme. The ACyc domain dimer of CyaB1 was modeled based upon the PDB structure 1wc5. See FIG. 5C.

Based on the analysis of distances between the C-termini of the α-helices in the PAS-GAF-PHY homodimer and the N-termini of the ACyc homodimer, an approximate fusion point is chosen (FIG. 9, MAQRTRAERK EVT SEQ ID NO:8). A library of PAS-GAF-PHY fusions to the ACyc domain of Nostoc sp. CyaB1 was constructed using one fixed site in the ACyc domain (FIG. 9) and variable (by a single amino acid) lengths of the α-helixes extending from the PHY domain of the photosensory module of BphG. These fusions were expressed in *E. coil* BL21 cya (pBphG) from an IPTG-inducible promoter.

The fusions were plated in the dark with no IPTG, and subsequently screened on a medium containing low and high levels of IPTG, in the absence (foil-wrapped plates) or presence of far-red (650 nm) light provided by LED panels. A set of the fusions with variable length linkers is shown in FIG. 9, where proteins are designated RlaC (red light-activated adenylyl cyclase). We identified four classes of fusion proteins;

(a) constitutively active (e.g., RlaC28), (b) constitutively inactive (or nonfunctional, e.g., RlaC15), (c) light-inactivated (e.g., RlaC18), and the desired class of (d) light-activated fusions (e.g., RlaC29, 17, 22, and 25). Analysis of these fusions revealed several important findings. First, we learned that a starting point for creating photoactivated fusions should be based on approximately the same distance (in three-dimensional space) between the helices extending from the PHY domains and between N-termini of the output domains. These distances are derived from structural models (or crystal structures). Second, photoactivated fusion proteins can be obtained at different boundaries of the output domains (however, not all). Therefore, multiple fusion sites should be tested to identify optimal fusions. Importantly, our data are consistent with the signaling helix rotation mechanism of bacteriophytochrome photoactivation. In accord with this mechanism, fusions differing by a complete α-helical turn (i.e., approximately 3.6 aa) position output domains in the same phase of the helix, and thus α-helices differing in length by 3 or 4 amino acids (aa) should have enzymatic activities that respond to light in a similar manner. This is exactly what we observed. For example, all photoactive forms shown in FIG. 2 differ from each other by 3 or 4 aa, i.e., close to a helical turn: RlaC29=RlaC17+4 aa; RlaC25=RlaC17−4 aa, and RlaC22=RlaC17−3 aa (FIG. 9).

First-generation near-infrared light-activated adenylyl cyclases shown in FIG. 9 show useful photoactivation ratios (~5.5-fold for RlaC25, according to the in vitro activity measurements (FIGS. 7 and 8C). To improve the photoactivation ratios and decrease adenylyl cyclase activity in the dark, error-prone PCR-based mutagenesis using the full-length rlaC25 gene as a template (at the mutation frequency of 3-4 mutations per gene) can be undertaken.

Substrate specificity in class III nucleotidyl cyclases depends on just a few residues (Winger et al., 2008). We have verified this hypothesis by converting the blue-light-activated adenylyl cyclase, BlaC, into a guanylyl cyclase, BlgC (Ryu et al., 2010) using as few as three mutations.

The RlaC and RlgC derivatives are purified and characterized in vitro using methods described by us earlier (Tarutina et al., 2006; Barends et al., 2009; Ryu et al., 2010). The sequences of these mutants are analyzed to elucidate the underlying causes of lower dark activity and higher photoactivation ratios.

Example 2

Engineering a Near-Infrared Light-Activated Executioner Caspase

Executioner caspases are terminal apoptosis-inducing proteases. They catalyze cleavage of essential cellular proteins thus irreversibly leading to apoptosis (reviewed in Crawford & Wells, 2011). Photoactivated executioner caspases can thus be used to induce specific spatiotemporal apoptosis to study molecular and cellular topics in animal development or disease. Caspase-3 functions as homodimer (reviewed in Mackenzie & Clay, 2008). In order to gain proteolytic activity, procaspase-3 undergoes proteolytic activation carried out by the upstream initiator caspases. However, Clark et al. constructed a noncleavable mutant D9A D28A D175A (designated D3A). An additional mutation, V266E, makes procaspase-3 active without proteolytic processing. The V266E mutant protein has a 60-fold higher enzymatic activity compared to the procaspase-3 D3A (which is inactive), and approximately ⅓ of the activity of the fully processed (active) caspase-3 (Pop et al., 2003; Walters et al., 2009). Since the procaspase-3 D3A V266E homodimer is intrinsically active, a distorted homodimer interface in the dark can be engineered, and restored by the light-induced helix rotation. This is conceptually identical to the task of engineering NIR light activated adenylyl cyclase.

The screening system developed by Hayashi et al. (Hayashi et al., 2009) for high throughput screening of DNA libraries in *Saccharomyces cerevisiae* is used for screening of photoactivated procaspase-3 fusions. In this system, the (pro) caspase-3 activity is monitored in yeast using a blue/white colony screening based on the level of expression of the lacZ reporter. Expression of the lacZ reporter gene is dependent on the transcription activator whose cellular localization is determined by the caspase-3 activity. If caspase-3 is active, the transcription activator is cleaved off from its transmembrane domain, released from the membrane, moves to the nucleus and activates lacZ expression. If caspase activity is low, the transcription activator remains as a fusion with the transmembrane domain and therefore is sequestered to the membrane and unable to activate lacZ expression. Active caspase-3 releases the transcription activator by cleaving at its recognition site, DEVD, engineered between the transmembrane and activator modules of the transcription activator. In addition to lacZ, LEU2 (providing for leucine prototrophy when expressed in the *S. cerevisiae* LEU2 mutant) can also be used as a reporter of caspase-3 activity.

The procaspase-3 D3A V266E is fused to the photoreceptor PAS-GAF-PHY module of BphG and expressed in *S. cerevisiae* under the galactose-inducible GAL1 promoter, in a dose-dependent fashion with the varying galactose concentration in the media. The photoactivated caspase-3 derivatives are identified as blue color colonies on X-gal leucine-deficient media on plates grow in the light. Responsiveness of such colonies to light is subsequently investigated upon comparing colony color in the light and in the dark as shown for photoactivated adenylyl cyclase (FIG. 7). The yeast strain also expresses the *R. sphaeroides* heme oxygenase BphO1 that provides biliverdin to the chimeric caspase.

First-generation photoactivated caspases identified are subjected to iterative mutagenesis and screening to identify those with the lowest dark activities and the highest photoactivation ratios (similar to those described for the photoactivated adenylyl cyclase). The optimized photoactivated procaspase-3 D3A V266E proteins are purified via the G-terminal His6-tag (Pop et al., 2003), and assayed in vitro using commercially available fluorescence- or chromogenic assays of caspase-3 activity.

Optimized versions of the photoactivated chimeric enzymes, adenylyl- and guanylyl cyclases and procaspase-3 can be expressed under cell- or tissue-specific promoters and delivered to desired organisms via gene delivery procedures known in the art by those of ordinary skill in the art without undue experimentation.

This work has shown for the first time the engineering of a near-infrared light-activated heterologous activities based on bacteriophytochrome photoreceptor modules, revealed engineering principles applicable to a variety of homodimeric proteins, and demonstrated the utility of random mutagenesis and screening in test organisms for identifying bacteriophytochrome-based proteins with improved photoactivation ratios and low dark activities.

The methods provided herein have been described in terms of specific illustrations. It will be appreciated by those of ordinary skill in the art that reagents, starting materials, and process steps and conditions can be varied without undue experimentation by substitution of equivalents thereto to achieve analogous results and produce analogous fusion proteins and DNA encoding them. All such variations are considered equivalent to those specifically illustrated herein, and are intended to be covered the claims hereof.

References

Adamantidis A R, Zhang F, Aravanis A M, Deisseroth K and de Lecea L. 2007. Neural substrates of awakening probed with optogenetic control of hypocretin neurons. *Nature* 450, 420-424

Airan R D, Thompson K R, Fenno L E, Bernstein H, Deisseroth K. 2009. Temporally precise in vivo control of intracellular signaling. *Nature* 458, 1025 1029

Barends, T. R. M., E. Hartmann, J. Griese, N. V. Kirienko, D. A. Ryjenkov, J. Reinstem, R. L. Shoeman, M. Gomelsky, I. Schlichting. 2009. Structure and mechanism of a light-regulated cyclic nucleotide phosphodiesterase. *Nature* 459, 1015-1018

Bhoo, S-H, Davis, S J, Walker, J., Karniol B, Vierstra R. 2001. Bacteriophytochromes are photochromic histidine kinases using a biliverdin chromophore, Nature 414, 776-779

Bulina M E, Chudakov D M, Britanova O V, Yanushevich Y G, Staroverov D B, Chepurnykh T V, Merzlyak E M, Shkrob M A, Lukyanov S, Lukyanov K A. 2006 A genetically encoded photosensitizer. *Nat Biotechnol* 24, 95-9

Bruder, S., J. U. Linder, S. E. Martinez, N. Zheng, J. A. Beavo, and J. E. Schultz. 2005. The cyanobacterial tandem GAF domains from the CyaB2 adenylyl cyclase signal via both cAMP-binding sites. *Proc Natl Acad Sci USA.* 102, 3088-92

Byrnes K R, Waynant R W, Ilev I K, Wu X, Barna L, Smith K, Heckert R, Gerst H, Anders J J. 2005. Light promotes regeneration and functional recovery and alters the immune response after spinal cord injury. *Lasers Surg Med.* 36, 171-85

Cardin J A, Carlén M, Meletis K, Knoblich U, Zhang F, Deisseroth K, Tsai L H and Moore C I. 2009. Driving fast-spiking cells induces gamma rhythm and controls sensory responses. *Nature* 459, 663-667

Cho M-H, Yoo Y, Bhoo S-H, Lee, S-W. 2011. Purification and characterization of a recombinant bacteriophytochrome of Xanthomonas oryzae pathovar oryzae. *Protein J* 30, 124-131

Crawford E D and Wells J A. 2011. Caspase substrates and cellular remodeling. *Annu Rev Biochemistry* 80, 1055-1087

Cubeddu R, Pifferi A, Taroni P, Torricelli A, Valentini G. 1999. Noninvasive absorption and scattering spectroscopy of bulk diffusive media: An application to the optical characterization of human breast. *Appl Phys Lett* 74, 874-6

De N, Navarro M V, Raghavan R V, Sondermann H. 2009. Determinants for the activation and autoinhibition of the diguanylate cyclase response regulator WspR. *J Mol Biol* 393, 619-633

De N, Pirruccello M, Krasteva P V, Bae N, Raghavan R V, Sondermann H. 2008. Phosphorylation-independent regulation of the diguanylate cyclase WspR. *PLoS Biol* 6, e67

Desmet K D, Paz D A, Corry J J, Eells J T, Wong-Riley M T, Henry M M, Buchmann E V, Connelly M P, Dovi J V, Liang H L, Henshel D S, Yeager R L, Millsap D S, Lim J, Gould L J, Das R, Jett M, Hodgson B D, Margolis D, Whelan H T. 2006. Clinical and experimental applications of NIR-LED photobiomodulation. *Photomed Laser Surg* 24, 121-128

Fang Q, Carp S A, Selb J, Boverman G, Zhang Q, Kopans D B, Moore R H, Miller E L, Brooks D H, Boas D A. 2009. Combined optical imaging and mammography of the healthy breast: optical contrast derived from breast structure and compression. *IEEE Trans Med Imaging* 28, 30-42

Georgianna W E, Deiters A. 2010. Reversible light switching of cell signaling by genetically encoded protein dimerization. *Chembiochem* 11, 301-3.

Gomelsky, M and Hoff W H. 2011. Light helps bacteria make important lifestyle decisions. *Trends Microbiol* 19, 441-8.

Gradinaru V, Mogri M, Thompson K R, Henderson J M and Deisseroth K. 2009. Optical deconstruction of parkinsonian neural circuitry. *Science* 324, 354-359

Gradinaru V, Zhang F, Ramakrishnan C, Mattis J, Prakash R, Diester I, Goshen I, Thompson K R, Deisseroth K. 2010. Molecular and cellular approaches for diversifying and extending optogenetics. *Cell* 141, 154-65

Hayashi H, Cuddy M, Shu V C, Yip K W, Madiraju C, Diaz P, Matsuyama T, Kaibara M, Taniyama K, Vasile S, Sergienko E, Reed J C. 2009. Versatile assays for high throughput screening for activators or inhibitors of intracellular proteases and their cellular regulators. PLoS One 4, e7655

Iseki M, Matsunaga S, Murakami A, Ohno K, Shiga K, Yoshida K, Sugai M, Takahashi T, Hori T, Watanabe M. 2002. A blue-light-activated adenylyl cyclase mediates photoavoidance in Euglena gracilis. Nature. 415, 1047-51

Jacobson K, Rajfur Z, Vitriol E and Klaus H. Chromophore-assisted laser inactivation in cell biology. *Trends Cell Biology* 18, 434-450

Kehoe, et al. Apr. 15, 2010. US Patent Publication No. US 2010/0093051 for "Light Regulated Transcription System For Use In Prokaryotic Organisms Kuzin A, Chen Y, Seetharaman J, Mao M, Xiao R, Ciccosanti C, Foote E L, Wang H, Everett J K, Nair R, Acton T B, Rost B, Montelione G T, Tong L, Hunt J F. X-Ray Structure of Protein (EAL/GGDEF domain protein) from M. capsulatus, Northeast Structural Genomics Consortium Target McR174c (2009). PDB 3ICL.

Landry Y, Niederhoffer N, Sick E, Gies J P. Heptahelical and other Gprotein-coupled receptors (GPCRs) signaling. *Curr Med Chem* 2006, 13:51-63

Leung D W, Otomo C, Chory J, Rosen M K. 2008 Genetically encoded photoswitching of actin assembly through the Cdc42-WASP-Arp2/3 complex pathway. *Proc Natl Acad Sci USA.* 105, 12797-802

Levskaya A, Weiner O D, Lim W A, Voigt C A. 2009; Spatiotemporal control of cell signaling using a light-switchable protein interaction. *Nature* 461, 997-1001

Levskaya A, Chevalier A A, Tabor J J, Simpson Z B, Lavery L A, Levy M, Davidson E A, Scouras A, Ellington A D, Marcotte E M, Voigt C A. 2005. Synthetic biology: engineering Escherichia coli to see light. *Nature* 438, 441-442

Li P, Gao X-G, Arellano R O, Renugopalakrishnan V. 2001. Glycosylated and Phosphorylated Proteins—Expression in Yeast and Oocytes of Xenopus: Prospects and Challenges—Relevance to Expression of Thermostable Proteins. *Protein Expression and Purification,* 22, 369-380

Liu X and Tonegawa S. 2010. Optogenetics 3.0. *Cell* 141, 22-24

Mackenzie S H and Clay C. 2008. Targeting cell death in tumors by activating caspases. Curr Cancer Drg Targets 8, 190-209

Maheshwari S C, Khurana J P, Sopory S K. 1999. Novel light-activated protein kinases as key regulators of plant growth and development. J. Biosci. 24 No. 4 49-514

Miesenböck G. The optogenetic catechism. 2009. *Science* 326, 395-9

Mills E, Chen X, Pham E, Wong S S, and Truong K. 2012. Engineering a photoactivated caspase-7 for rapid induction of apoptosis. *ACS Synthetic Biol* 3, 75-82

Möglich A, Yang X, Ayers R A, Moffat K. 2010. Structure and function of plant photoreceptors. *Annu Rev Plant Biol* 61, 21-47

Möglich A, Ayers R A, Moffat K. 2009. Design and signaling mechanism of light-regulated histidine kinases. *J Mol Biol* 385, 1433-44

Möglich A, Moffat K. September 2010. Engineered photoreceptors as novel optogenetic tools. *Photochemical and Photobiological Sciences,* 9, 1286-1300

Pei J, Grishin N V. 2001. GGDEF domain is homologous to adenylyl cyclase. *Proteins.* 42, 210-216

Pop C., Feeney, A. Tripathy, and A. C. Clark. 2003. Mutations in the procaspase-3 dimer interface affect the activity of the zymogen. Biochemistry, 42, 12311-12320

Quail et al. 2005 U.S. Pat. No. 6,858,429 for Universal Light-Switchable Gene Promoter System Rockwell N C, Su Y S, Lagarias J C. 2006. Phytochrome structure and signaling mechanisms *Annu Rev Plant Biol.* 57, 837-858

Ryjenkov, D. A., M. Tarutina, O. V. Moskvin and M. Gomelsky. 2005. Cyclic diguanylate is a ubiquitous signaling molecule in bacteria: Insights into the biochemistry of the GGDEF protein domain. *J Bacteriol* 187, 1792-1798

Ryu, M.-H., O. V. Moskvin, J Siltberg-Liberles, and M. Gomelsky. 2011. Natural and engineered photoactivated nucleotidyl cyclases for optogenetic applications. *J Biol Chem* 2010 Oct. 28. [Epub ahead of print]

Schirmer T, Jenal U. 2009. Structural and mechanistic determinants of c-di-GMP signalling. *Nat Rev Microbiol* 7, 724-735

Serezani C H, Ballinger M N, Aronoff D M, Peters-Golden M. 2008. Cyclic AMP: master regulator of innate immune cell function. Am J Respir Cell Mol. Biol. 39, 127-32

Shu X, Royant A, Lin M Z, Aguilera T A, Lev-Ram Varda, Steinbach P A, Tsien R Y. 2009. Mammalian expression of infrared fluorescent proteins engineered from a bacterial phytochrome. *Science* 324, 804-7

Sinha S C, Sprang S R. 2006. Structures, mechanism, regulation and evolution of class III nucleotidyl cyclases. *Rev Physiol Biochem Pharmacol* 157, 105-140

Sjulson L and Miesenböck G. 2008. Photocontrol of neural activity: Biophysical mechanisms and performance in vivo. *Chem. Rev* 108, 1588-1602

Sohal V S, Zhang F, Yizhar O and Deisseroth K. 2009. Parvalbumin neurons and gamma rhythms enhance cortical circuit performance, *Nature* 459, 698-702

Sorokina O, Kapus A, Terecske K, Dixon L E, Kozma-Bognar L, Nagy F, and Millar A J. 2009. A switchable light-input, light-output system modelled and constructed in yeast. *Journal of Biological Engineering,* 3:15

Stierl M, Stumpf P, Udwari D, Gueta R, Hagedorn R, Losi A, Gartner W, Petereit L, Efetova M, Schwarzel M, Oertner T G, Nagel G, Hegemann P. Light modulation of cellular cAMP by a small bacterial photoactivated adenylyl cyclase, bPAC, of the soil bacterium *Beggiatoa. J Biol. Chem.* 2011, 286:1181-8

Strickland D, Moffat K, Sosnick T R. 2008. Light-activated DNA binding in a designed allosteric protein. *Proc Natl Acad Sci USA* 105, 10709-10714

Tarutina, M., Ryjenkov, D. A., and Gomelsky, M. 2006. An unorthodox bacteriophytochrome from *Rhodobacter sphaeroides* involved in turnover of the second messenger c-di-GMP. *J Biol Chem* 281, 34751-34758

Toettcher J E, Voigt C A, Weiner O D, and Lim W A. 2011. The promise of optogenetics in cell biology: interrogating molecular circuits in space and time. *Nature Methods* 8, 35-38

Tønnesen J, Sørensen A T, Deisseroth K, Lundberg C and Kokaia M. 2009. Optogenetic control of epileptiform activity, *Proc Natl Acad Sci USA* 106, 12162-12167

Tsai H C, Zhang F, Adarharitidis A, Stuber G D, Bond A, de Lecea L, and Deisseroth K. 2009. Phasic firing in dopaminergic neurons is sufficient for behavioral conditioning. *Science* 324, 1080-1084

Tyszkiewicz A B, Muir T W. 2008. Activation of protein splicing with light in yeast. *Nature Methods* 5, 303-305

Vera, Aris A, Daura X, Martinez M A, Villaverde A. 2005. Engineering the *E. coli* beta-galactosidase for the screening of antiviral protease inhibitors. *Biochem Biophys Res Commun* 329, 453-6

Vuillet L, Kojadinovic M, Zappa S, Jaubert M, Adriano J. M., Fardoux J I, Hannibal L, Pignol D, Vermeglio A, Giraud E. 2007. Evolution of a bacteriophytochrome from light to redox sensor. *EMBO Journal,* 26, 3322-3331

Walters J, Pop C, Scott F L, Drag M, Swartz P, Mattos C, Salvesen G S, Clark A C. 2009. A constitutively active and uninhibitable caspase-3 zymogen efficiently induces apoptosis. *Biochem J* 424, 335-45.

Wan S, Parrish J A, Anderson R R, Madden M. 1981. Transmittance of nonionizing radiation in human tissues. *Photochem Photobiol* 34, 679-81.

Weissleder R. 2001. A clearer vision for in vivo imaging. *Nature Biotechnol* 19, 316-7

Wu Y I, Frey D, Lungu O., Jaehrig A, Schlichting I, Kuhlman B, Hahn K M. 2009. A genetically encoded photoactivatable Rac controls the motility of living cells. *Nature* 461, 104-108

Yang X, Kuk J, Moffat K. 2008. Crystal structure of *Pseudomonas aeruginosa* bacteriophytochrome: photbconversion and signal transduction. *Proc Natl Acad Sci USA* 105, 14715-14720

Yang X, Kuk J, Moffat K. 2009. Conformational differences between the Pfr and Pr states in *Pseudomonas aeruginosa* bacteriophytochrome. *Proc Natl Acad Sci USA* 106, 15639-15644

Yazawa M, Sadaghiani A M, Hsueh B, Dolmetsch R E. 2009. Induction of protein-protein interactions in live cells using light. *Nat Biotechnol* 27, 941-945

Zimmer M. 2009. GFP: from jellyfish to the Nobel prize and beyond. *Chem Soc Rev* 38, 2823-2832

The invention claimed is:

1. A method for producing photoactive fusion proteins having a desired activity controllable by far-red and/or near-infrared (NIR) light, said method comprising the steps:
   a. designing one or more homodimeric fusion proteins, each comprising a photoreceptor protein module and a heterologous output module, wherein:
      i. said homodimeric fusion proteins comprise two monomers that each comprise:
         (1) a photoreceptor module of a bacteriophytochrome; and
         (2) a heterologous output module capable of being activated upon homodimerization to perform said desired activity; and
      ii. said monomers are not active when separated, but are capable of combining to form homodimers that are controllable by NIR light:
      wherein designing said fusion proteins comprises identifying candidate output domains based on 3D structures or models, identifying candidate protein fusion sites and estimating lengths of a-helices linking said output modules to said photosensory modules;
   b. producing a plurality of DNA molecules, each encoding a said monomer of a said homodimeric fusion protein that has at least one unique fusion site;
   c. screening said DNA molecules for their ability to produce homodimeric photoactive fusion proteins capable of performing said desired activity by a method comprising:
      i. transforming a designed non-human test organism with a plurality of different said DNA molecules such that a different said fusion protein is expressed in each test organism;
      ii. allowing the expressed fusion proteins to bind bacteriophytochrome chromophore and form homodimeric proteins; and
      iii. applying selected wavelengths of NIR light to said transformed organisms and determining the level of said desired activity of said fusion proteins in said organisms in the presence and absence of said selected wavelengths of light;
   wherein the level of said desired activity of said fusion proteins is controllable by NIR light when the level of said desired activity is changed by the presence and/or absence of MR light having said selected wavelengths.

2. The method of claim 1 for producing fusion proteins with enhanced controllability by NIR light, wherein such enhanced controllability exists when said fusion proteins have high ratios of activity in the light versus dark or vice versa.

3. The method of claim 1 also comprising transforming said test organisms with DNA encoding a heme oxygenase gene capable of being expressed in said test organisms to produce a biliverdin IXα chromophore.

4. The method of claim 3 wherein said test organisms do not comprise an endogenous chromophore.

5. The method of claim 1 wherein said test organisms comprise an endogenous chromophore.

6. The method of claim 1 also comprising modifying the design of said fusion proteins that are controllable by NIR light to produce additional candidate fusion proteins by designing additional fusion sites and linkers for said fusion proteins and repeating the steps of producing DNA encoding the additional fusion proteins, transforming suitable organisms with this DNA, expressing the DNA, and screening the resultant fusion proteins for additional fusion proteins controllable by NIR light.

7. The method of claim 6 wherein said linker lengths are increased or decreased by the length of one or more helical turns to produce said additional candidate fusion proteins.

8. The method of claim 7 wherein said linker lengths are increased or decreased by three or four amino acids.

9. The method of claim 1 wherein said fusion proteins controllable by NIR light, or additional fusion proteins controllable by NIR light produced by increasing or decreasing their linker lengths, are mutagenized to create further candidate fusion proteins controllable by NIR light, and said screen steps are repeated to screen for further photoactivated fusion proteins.

10. The method of claim 1 wherein said bacteriophytochrome photoreceptor module is from the BphG1 protein from *Rhodobacter sphaeroides*.

11. The method of claim 1 wherein said suitable organism for expression of said fusion protein is a cultured organism selected from the group consisting of *E. coli*, yeast, plant, or mammalian cells selected or modified so as to detectably exhibit the level of activity of said expressed fusion protein controllable by the presence or absence of NIR light.

12. The method of claim 1 wherein said fusion protein is a light-responsive nucleotidyl cyclase or light-responsive uncleavable procaspase-3.

13. The method of claim 1 wherein said desired activity is increased by the application of NIR light of a selected wavelength.

14. The method of claim 1 wherein said desired activity is decreased by the application of NIR light of a selected wavelength.

15. The method of claim 1 wherein said desired activity is gradually decreased or gradually increased by ceasing to apply NIR light of a selected wavelength.

16. The method of claim 1 wherein said desired activity is immediately increased or decreased by the application of NIR light of a selected wavelength.

* * * * *

SEQUENCE LISTING

<160> NUMBER OF SEQ ID NOS: 13

<210> SEQ ID NO 1
<211> LENGTH: 22
<212> TYPE: PRT
<213> ORGANISM: Artificial

```
<220> FEATURE:
<223> OTHER INFORMATION: Transformed E. coli linker sequence

<400> SEQUENCE: 1

Met Ala Gln Arg Thr Arg Ala Glu Leu Ala Arg Leu Arg His Tyr Asp
1               5                   10                  15

Glu Arg Lys Glu Val Thr
            20

<210> SEQ ID NO 2
<211> LENGTH: 19
<212> TYPE: PRT
<213> ORGANISM: Artificial
<220> FEATURE:
<223> OTHER INFORMATION: Transformed E. coli linker sequence

<400> SEQUENCE: 2

Met Ala Gln Arg Thr Arg Ala Glu Leu Ala Arg Leu Arg Glu Arg Lys
1               5                   10                  15

Glu Val Thr

<210> SEQ ID NO 3
<211> LENGTH: 18
<212> TYPE: PRT
<213> ORGANISM: Artificial
<220> FEATURE:
<223> OTHER INFORMATION: Transformed E. coli linker sequence

<400> SEQUENCE: 3

Met Ala Gln Arg Thr Arg Ala Glu Leu Ala Arg Leu Glu Arg Lys Glu
1               5                   10                  15

Val Thr

<210> SEQ ID NO 4
<211> LENGTH: 17
<212> TYPE: PRT
<213> ORGANISM: Artificial
<220> FEATURE:
<223> OTHER INFORMATION: Transformed E. coli linker sequence

<400> SEQUENCE: 4

Met Ala Gln Arg Thr Arg Ala Glu Leu Ala Arg Glu Arg Lys Glu Val
1               5                   10                  15

Thr

<210> SEQ ID NO 5
<211> LENGTH: 16
<212> TYPE: PRT
<213> ORGANISM: Artificial
<220> FEATURE:
<223> OTHER INFORMATION: Transformed E. coli linker sequence

<400> SEQUENCE: 5

Met Ala Gln Arg Thr Arg Ala Glu Leu Ala Glu Arg Lys Glu Val Thr
1               5                   10                  15

<210> SEQ ID NO 6
<211> LENGTH: 15
<212> TYPE: PRT
<213> ORGANISM: Artificial
<220> FEATURE:
<223> OTHER INFORMATION: Transformed E. coli linker sequence
```

-continued

<400> SEQUENCE: 6

Met Ala Gln Arg Thr Arg Ala Glu Leu Glu Arg Lys Glu Val Thr
1               5                   10                  15

<210> SEQ ID NO 7
<211> LENGTH: 14
<212> TYPE: PRT
<213> ORGANISM: Artificial
<220> FEATURE:
<223> OTHER INFORMATION: Transformed E. coli linker sequence

<400> SEQUENCE: 7

Met Ala Gln Arg Thr Arg Ala Glu Glu Arg Lys Glu Val Thr
1               5                   10

<210> SEQ ID NO 8
<211> LENGTH: 13
<212> TYPE: PRT
<213> ORGANISM: Artificial
<220> FEATURE:
<223> OTHER INFORMATION: Transformed E. coli linker sequence

<400> SEQUENCE: 8

Met Ala Gln Arg Thr Arg Ala Glu Arg Lys Glu Val Thr
1               5                   10

<210> SEQ ID NO 9
<211> LENGTH: 12
<212> TYPE: PRT
<213> ORGANISM: Artificial
<220> FEATURE:
<223> OTHER INFORMATION: Transformed E. coli linker sequence

<400> SEQUENCE: 9

Met Ala Gln Arg Thr Arg Glu Arg Lys Glu Val Thr
1               5                   10

<210> SEQ ID NO 10
<211> LENGTH: 11
<212> TYPE: PRT
<213> ORGANISM: Artificial
<220> FEATURE:
<223> OTHER INFORMATION: Transformed E. coli linker sequence

<400> SEQUENCE: 10

Met Ala Gln Arg Thr Glu Arg Lys Glu Val Thr
1               5                   10

<210> SEQ ID NO 11
<211> LENGTH: 10
<212> TYPE: PRT
<213> ORGANISM: Artificial
<220> FEATURE:
<223> OTHER INFORMATION: Transformed E. coli linker sequence

<400> SEQUENCE: 11

Met Ala Gln Arg Glu Arg Lys Glu Val Thr
1               5                   10

<210> SEQ ID NO 12
<211> LENGTH: 9
<212> TYPE: PRT
<213> ORGANISM: Artificial
<220> FEATURE:
<223> OTHER INFORMATION: Transformed E. coli linker sequence

```
<400> SEQUENCE: 12

Met Ala Gln Glu Arg Lys Glu Val Thr
1               5

<210> SEQ ID NO 13
<211> LENGTH: 8
<212> TYPE: PRT
<213> ORGANISM: Artificial
<220> FEATURE:
<223> OTHER INFORMATION: Transformed E. coli linker sequence

<400> SEQUENCE: 13

Met Ala Glu Arg Lys Glu Val Thr
1               5
```